United States Patent [19]
Albrecht et al.

[11] Patent Number: 6,013,445
[45] Date of Patent: Jan. 11, 2000

[54] MASSIVELY PARALLEL SIGNATURE SEQUENCING BY LIGATION OF ENCODED ADAPTORS

[75] Inventors: Glenn Albrecht, Redwood City, Calif.; Sydney Brenner, Cambridge, United Kingdom; Robert B. DuBridge, Belmont, Calif.; David H. Lloyd, Daly City, Calif.; Michael C. Pallas, San Bruno, Calif.

[73] Assignee: Lynx Therapeutics, Inc., Hayward, Calif.

[21] Appl. No.: 08/946,138

[22] Filed: Oct. 7, 1997

Related U.S. Application Data

[63] Continuation-in-part of application No. 08/862,610, May 23, 1997, abandoned, which is a continuation-in-part of application No. 08/689,587, Aug. 12, 1996, abandoned, which is a continuation-in-part of application No. 08/659,453, Jun. 6, 1996, abandoned.

[51] Int. Cl.$^7$ .............................. C12Q 1/68; C07H 21/02
[52] U.S. Cl. .............................................. 435/6; 536/24.2
[58] Field of Search .................. 435/6, 91.52; 536/24.2, 536/24.3, 26.6; 935/77, 78

[56] References Cited

U.S. PATENT DOCUMENTS

| | | | |
|---|---|---|---|
| 4,237,224 | 12/1980 | Cohen et al. | 435/68 |
| 4,293,652 | 10/1981 | Cohen | 435/172 |
| 4,321,365 | 3/1982 | Wu et al. | 536/27 |
| 4,683,202 | 7/1987 | Mullis | 435/91 |
| 4,775,619 | 10/1988 | Urdea | 435/6 |
| 4,942,124 | 7/1990 | Church | 435/6 |
| 5,093,245 | 3/1992 | Keith et al. | 435/91 |
| 5,102,785 | 4/1992 | Livak et al. | 435/6 |
| 5,118,605 | 6/1992 | Urdea | 435/6 |
| 5,126,239 | 6/1992 | Livak et al. | 435/6 |
| 5,149,625 | 9/1992 | Church et al. | 435/6 |
| 5,242,794 | 9/1993 | Whiteley et al. | 435/6 |
| 5,366,860 | 11/1994 | Bergot et al. | 435/6 |
| 5,503,980 | 4/1996 | Cantor | 435/6 |
| 5,508,169 | 4/1996 | Deugau et al. | 435/6 |
| 5,512,439 | 4/1996 | Hornes et al. | 435/6 |
| 5,552,278 | 9/1996 | Brenner | 435/6 |
| 5,599,675 | 2/1997 | Brenner | 435/6 |
| 5,604,097 | 2/1997 | Brenner | 435/6 |
| 5,658,736 | 8/1997 | Wong | 435/6 |
| 5,707,807 | 1/1998 | Kato | 435/6 |
| 5,714,330 | 2/1998 | Brenner et al. | 435/6 |
| 5,728,524 | 3/1998 | Sibson | 435/6 |

FOREIGN PATENT DOCUMENTS

| | | |
|---|---|---|
| 0 246 864 B1 | 11/1987 | European Pat. Off. . |
| 0 303 459 A3 | 2/1989 | European Pat. Off. . |
| 0 392 546 A2 | 10/1990 | European Pat. Off. . |
| 0 799 897 A1 | 10/1997 | European Pat. Off. . |
| 2 687 851 | 5/1994 | France . |
| WO92/15712 | 9/1992 | WIPO . |
| WO94/01582 | 1/1994 | WIPO . |
| WO95/20053 | 7/1995 | WIPO . |
| WO96/12014 | 4/1996 | WIPO . |

OTHER PUBLICATIONS

Brenner and Livak, "DNA fingerprinting by sampled sequencing," Proc. Natl. Acad. Sci., 86: 8902–8906 (1989).
Carrano et al, "A high–resolution, fluorescence–based semi–automated method for DNA fingerprinting," Genomics, 4: 129–136 (1989).
Szybalski et al, "Class–IIS restriction enzymes—a review," Gene, 100: 13–26 (1991).
Kim et al, "Cleaving DNA at any predetermined site with adapter–primers and Class IIS restriction enzymes," Science, 240:504–506 (1988).
Szybalski, "Universal restriction endonucleases: designing novel cleavage specificities by combining adapter oligonucleotide and enzyme moieties," Gene, 40: 169–173 (1985).
Barany, "The ligase chain reaction in a PCR world," PCR Methods and Applications, 1: 5–16 (1991).
Wu and Wallace, "The ligase amplification reaction (LAR)—amplification of specific DNA sequences using sequential rounds of template–dependent ligation," Genomics, 4: 560–569 (1989).
McGuigan et al, "DNA fingerprinting by sampled sequencing," Methods in Enzymology, 218: 241–258 (1993).
Shoemaker et al, "Quantitative phenotypic analysis of yeast deletion mutants using a highly parallel molecular bar–coding strategy," Nature Genetics, 14: 450–456 (1996).
Kato, "Description of the entire mRNA population by a 3' end cDNA fragment generated by class IIs restriction enzymes," Nucleic Acids Research, 23: 3685–3690 (1995).
Kato, "RNA fingerprinting by molecular indexing," Nucleic Acids Research, 24: 394–395 (1996).
Broude et al, "Enhanced DNA sequencing by hybridization," Proc. Natl. Acad. Sci., 91: 3072–3076 (1994).
Hultman et al, "Direct solid phase sequencing of genomic and plasmid DNA using magnetic beads as solid support," Nucleic Acids Research, 17: 4937–4946 (1989).
Nikiforov et al, "Genetic bit analysis: a solid phase method for typing single nucleotide polymorphisms," Nucleic Acids Research, 22: 4167–4175 (1994).
Berger, "Expanding the potential of restriction endonucleases: use of hapaxoterministic enzymes," Anal. Biochem., 222: 1–8 (1994).
Unrau et al, "Non–cloning amplification of specific DNA fragments from whole genomic DNA digests using DNA 'indexers,'" Gene, 145: 163–169 (1994).

(List continued on next page.)

*Primary Examiner*—Eggerton A. Campbell
*Attorney, Agent, or Firm*—Stephen C. Macevicz

[57] ABSTRACT

The invention provides a method of nucleic acid sequence analysis based on the ligation of one or more sets of encoded adaptors to the terminus of a target polynucleotide. Encoded adaptors whose protruding strands form perfectly matched duplexes with the complementary protruding strands of the target polynucleotide are ligated, and the identity of the nucleotides in the protruding strands is determined by an oligonucleotide tag carried by the encoded adaptor. Such determination, or "decoding" is carried out by specifically hybridizing a labeled tag complement to its corresponding tag on the ligated adaptor.

29 Claims, 10 Drawing Sheets

OTHER PUBLICATIONS

Gronostajski, "Site–specific DNA binding of nuclear factor I: effect of the spacer region," Nucleic Acids Research, 15: 5545–5559 (1987).

Wiaderkiewicz et al, "Mismatch and blunt to protuding end joining by DNA ligases," Nucleic Acids Research, 15: 7831–7848 (1987).

Tsiapalis et al, "On the fidelity of phage T4–induced polynucleotide ligase in the joining of chemically synthesized deoxyribooligonucleotides," Biochem. Biophys. Res. Comm., 39:631–636 (1970).

Matteucci et al, "Targeted random mutagenesis: the use of ambigously synthesized oligonucleotides to mutagenize sequences immediately 5' of an ATG initiation condon," Nucleic Acids Research, 11: 3113–3121 (1983).

Hensel et al, "Simultaneous identification of bacterial virulence genes by negative selection," Science, 269: 400–403 (1995).

Cleave with $A_3$ endonuclease & Ligate third set of encoded probes (42)

MASSIVELY PARALLEL SIGNATURE SEQUENCING BY LIGATION OF ENCODED ADAPTORS

This is a continuation-in-part of abandoned U.S. patent application Ser. No. 08/862,610 filed May 23, 1997, which is a continuation-in-part of abandoned U.S. patent application Ser. No. 08/689,587 filed Aug. 12, 1996, which is a continuation-in-part of abandoned U.S. patent application Ser. No. 08/659,453 filed Jun. 6, 1996.

FIELD OF THE INVENTION

The invention relates generally to methods for determining the nucleotide sequence of a polynucleotide, and more particularly, to a method of identifying terminal nucleotides of a polynucleotide by specific ligation of encoded adaptors.

BACKGROUND

The DNA sequencing methods of choice for nearly all scientific and commercial applications are based on the dideoxy chain termination approach pioneered by Sanger, e.g. Sanger et al, Proc. Natl. Acad. Sci., 74: 5463–5467 (1977). The method has been improved in several ways and, in a variety of forms, is used in all commercial DNA sequencing instruments, e.g. Hunkapiller et al, Science, 254: 59–67 (1991).

The chain termination method requires the generation of one or more sets of labeled DNA fragments, each having a common origin and each terminating with a known base. The set or sets of fragments must then be separated by size to obtain sequence information. The size separation is usually accomplished by high resolution gel electrophoresis, which must have the capacity of distinguishing very large fragments differing in size by no more than a single nucleotide. Despite many significant improvements, such as separations with capillary arrays and the use of non-gel electrophoretic separation mediums, the technique does not readily lend itself to miniaturization or to massively parallel implementation.

As an alternative to the Sanger-based approaches to DNA sequencing, several so-called "base-by-base" or "single base" sequencing approaches have been explored, e.g. Cheeseman, U.S. Pat. No. 5,302,509; Tsien et al, International application WO 91/06678; Rosenthal et al, International application WO 93/21340; Canard et al, Gene, 148: 1–6(1994); and Metzker et al, Nucleic Acids Research, 22: 4259–4267 (1994). These approaches are characterized by the determination of a single nucleotide per cycle of chemical or biochemical operations and no requirement of a separation step. Thus, if they could be implemented as conceived, "base-by-base" approaches promise the possibility of carrying out many thousands of sequencing reactions in parallel, for example, on target polynucleotides attached to microparticles or on solid phase arrays, e.g. International patent application PCT/US95/12678.

Unfortunately, "base-by-base" sequencing schemes have not had widespread application because of numerous problems, such as inefficient chemistries which prevent determination of any more than a few nucleotides in a complete sequencing operation. Moreover, in base-by-base approaches that require enzymatic manipulations, further problems arise with instrumentation used for automated processing. When a series of enzymatic steps are carried out in reaction chambers having high surface-to-volume ratios and narrow channel dimensions, enzymes may stick to surface components making washes and successive processing steps very difficult. The accumulation of protein also affects molecular reporter systems, particularly those employing fluorescent labels, and renders the interpretation of measurements based on such systems difficult and inconvenient. These and similar difficulties have significantly slowed the application of "base-by-base" sequencing schemes to parallel sequencing efforts.

An important advance in base-by-base sequencing technology could be made, especially in automated systems, if an alternative approach was available for determining the terminal nucleotides of polynucleotides that minimized or eliminated repetitive processing cycles employing multiple enzymes.

SUMMARY OF THE INVENTION

Accordingly, an object of our invention is to provide a DNA sequencing scheme which does not suffer the drawbacks of current base-by-base approaches.

Another object of our invention is to provide a method of DNA sequencing which is amenable to parallel, or simultaneous, application to thousands of DNA fragments present in a common reaction vessel.

A further object of our invention is to provide a method of DNA sequencing which permits the identification of a terminal portion of a target polynucleotide with minimal enzymatic steps.

Yet another object of our invention is to provide a set of encoded adaptors for identifying the sequence of a plurality of terminal nucleotides of one or more target polynucleotides.

Our invention provides these and other objects by providing a method of nucleic acid sequence analysis based on the ligation of one or more sets of encoded adaptors to a terminus of a target polynucleotide (or to the termini of multiple target polynucleotides when used in a parallel sequencing operation). Each encoded adaptor comprises a protruding strand and an oligonucleotide tag selected from a minimally cross-hybridizing set of oligonucleotides. Encoded adaptors whose protruding stands form perfectly matched duplexes with the complementary protruding strands of the target polynucleotide are ligated. After ligation, the identity and ordering of the nucleotides in he protruding strands are determined, or "decoded," by specifically hybridizing a labeled tag complement to its corresponding tag on the ligated adaptor.

For example, if an encoded adaptor with a protruding strand of four nucleotides, say 5'-AGGT, form a perfectly matched duplex with the complementary protruding strand of a target polynucleotide and is ligated, the four complementary nucleotides, 3'-TCCA, on the polynucleotide may be identified by a unique oligonucleotide tag selected form a set of 256 such tags, one for every possible four nucleotide sequence of the protruding strands. Tag complements are applied to the ligated adaptors under conditions which allow specific hybridization of only those tag complements that form perfectly matched duplexes (or triplexes) with the oligonucleotide tags of the ligated adaptors. The tag complements may be applied individually or as one or more mixtures to determine the identity of the oligonucleotide tags, and therefore, the sequences of the protruding strands.

As explain more fully below, the encoded adaptors may be used in sequence analysis either i) to identify one or more nucleotides as a step of a process that involves repeated cycles of ligation, identification, and cleavage, as described in Brenner U.S. Pat. No. 5,599,675, or ii) as a "stand alone" identification method, wherein sets of encoded adaptors are applied to target polynucleotides such that each set is capable of identifying the nucleotide sequence of a different portion of a target polynucleotide; that is, in the latter embodiment, sequence analysis is carried out with a single ligation for each set followed by identification.

An important feature of the encoded adaptors is the use of oligonucleotide tags that are members of a minimally cross-hybridizing set of oligonucleotides, e.g. as described in International patent applications PCT/US95/12791 and PCT/US96/09513. The sequences of oligonucleotides of such a set differ from the sequences of every other member of the same set by at least two nucleotides. Thus, each member of such a set cannot form a duplex (or triplex) with the complement of any other member with less than two mismatches. Preferably, each member of a minimally cross-hybridizing set differs from every other member by as much nucleotides as possible consistent with the size of set required for a particular application. For example, where longer oligonucleotide tags are used, such as 12- to 20-mers for delivering labels to encoded adaptors, then the difference between members of a minimally cross-hybridizing set is preferably significantly greater than two. Preferably, each member of such a set differs from every other member by at least four nucleotides. More preferably, each member of such a set differs from every other member by at least six nucleotides. Complements of oligonucleotide tags of the invention are referred to herein as "tag complements."

Oligonucleotide tags may be single stranded and be designed for specific hybridization to single stranded tag complements by duplex formation. Oligonucleotide tags may also be double stranded and be designed for specific hybridization to single stranded tag complements by triplex formation. Preferably, the oligonucleotide tags of the encoded adaptors are double stranded and their tag complements are single stranded, such that specific hybridization of a tag with its complements occurs through the formation of a triplex structure.

Preferably, the method of the invention comprises the following steps: (a) ligating an encoded adaptor to an end of a polynucleotide, the adaptor having an oligonucleotide tag selected from a minimally cross-hybridizing set of oligonucleotides and a protruding strand complementary to a protruding strand of the polynucleotide; and (b) identifying one or more nucleotides in the protruding strand of the polynucleotide by specifically hybridizing a tag complement to the oligonucleotide tag of the encoded adaptor.

DEFINITIONS

Figure 1A:
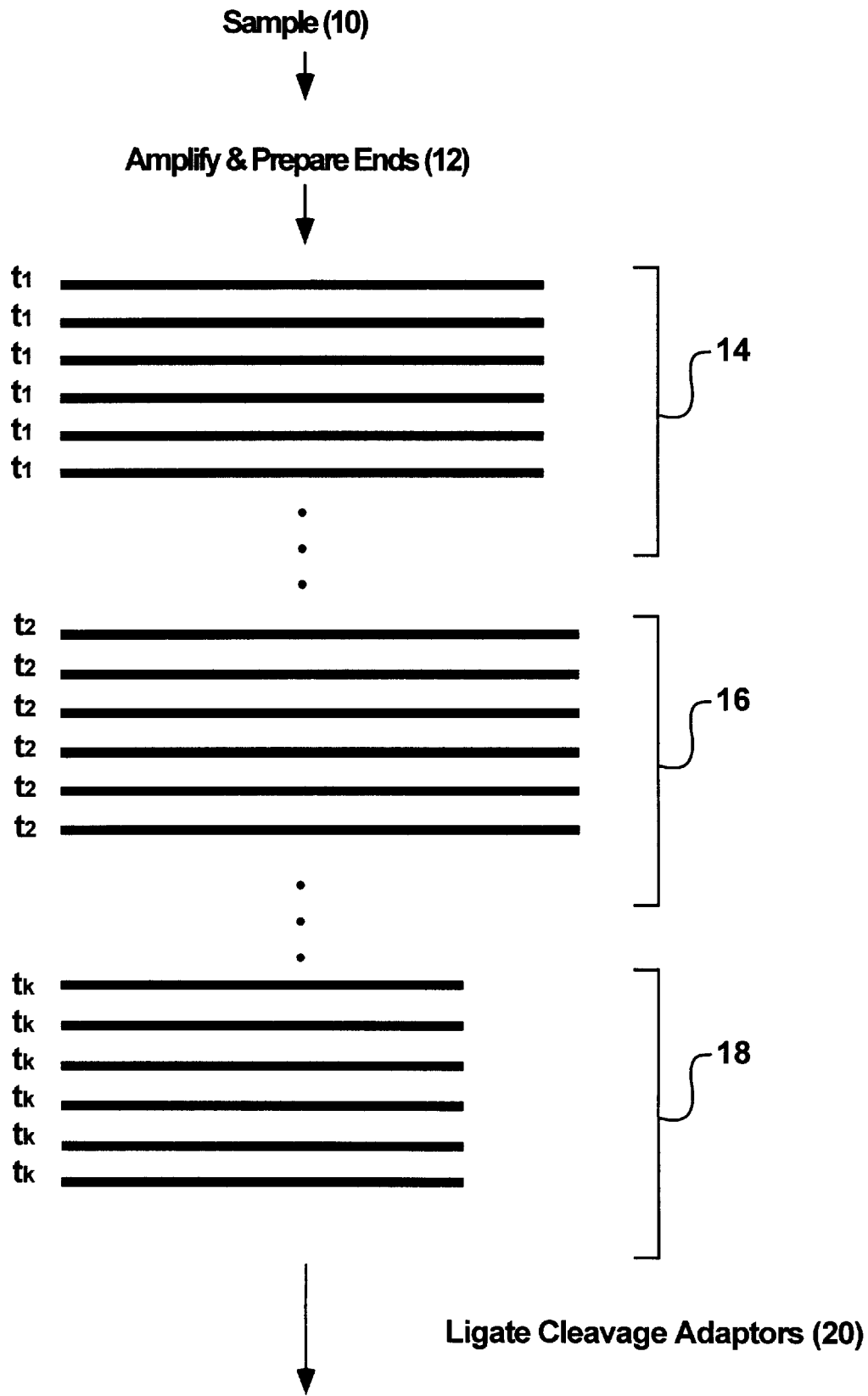
FIGS. 1a–1e diagrammatically illustrate the use of encoded adaptors to determine the terminal nucleotides sequences of a plurality of tagged polynucleotides.

As used herein, the term "encoded adaptor" is used synonymously with the term "encoded probe" of priority document U.S. patent application Ser. No. 08/689,587.

As used herein, the term "ligation" means the formation of a covalent bond between the ends of one or more (usually two) oligonucleotides. The term usually refers to the formation of a phosphodiester bond resulting from the following reaction, which is usually catalyzed by a ligase:

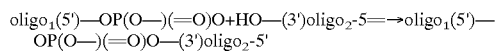

where $oligo_1$ and $oligo_2$ are either two different oligonucleotides or different ends of the same oligonucleotide. The term encompasses non-enzymatic formation of phosphodiester bonds, as well as the formation of non-phosphodiester covalent bonds between the ends of oligonucleotides, such as phosphorothioate bonds, disulfide bonds, and the like. A ligation reaction is usually template driven, in hat the ends of $oligo_1$ and $oligo_2$ are brought into juxtaposition by specific hybridization to a template strand. A special case of template-driven ligation is the ligation of two double stranded oligonucleotides having complementary protruding strands.

"Complement" or "tag complement" as used herein in reference to oligonucleotide tags refers to an oligonucleotide to which a oligonucleotide tag specifically hybridizes to form a perfectly matched duplex or triplex. In embodiment where specific hybridization results in a triplex, the oligonucleotide tag may be selected to be either double stranded or single stranded. Thus, where triplexes are formed, the term "complement" is meant to encompass either a double stranded complement of a single stranded oligonucleotide tag or a single stranded complement of a double stranded oligonucleotide tag.

The term "oligonucleotide" as used herein includes linear oligomers of natural or modified monomers or linkages, including deoxyribonucleosides, ribonucleosides, anomeric forms thereof, peptide nucleic acids (PNAs), and the like, capable of specifically binding to a target polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g. 3–4, to several tens of monomeric units, e.g. 40–60. Whenever an oligonucleotide is represented by a sequence of letters, such as "ATGCCTG," it will be understood that the nucleotides are in 5'→3' order from left to right and the "A" denotes deoxyadenosine, "C" denotes deoxycytidine, "G" denotes deoxyguanosine, an d"T" denotes thymidine, unless otherwise noted. Usually oligonucleotides of the invention comprise the four natural nucleotides; however, they may also comprise non-natural nucleotide analogs. It is clear to those skilled in the art when oligonucleotides having natural or non-natural nucleotides may be employed, e.g. where processing by enzymes is called for, usually oligonucleotides consisting of natural nucleotides are required.

"Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair of triplet of nucleotides in the duplex or triplex fails to undergo Watson-Crick and/or Hoogsteen and/or reverse Hoogsteen bonding.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543–584 (1990), or the like, with the only proviso that they are capable of specific hybridization. Such analogs include synthetic nucleosides designed to enhance binding properties, reduce complexity, increase specificity, and the like.

As used herein "sequence determination" or "determining a nucleotide sequence" in reference to polynucleotides includes determination of partial as well as full sequence information of the polynucleotide. That is, the term includes sequence comparisons, fingerprinting, and like levels of information about a target polynucleotide, as well as the express identification and ordering of nucleosides, usually each nucleoside, in a target polynucleotide. The term also includes the determination of the identification, ordering, and locations of one, two, or three of the four types of nucleotides within a target polynucleotide. For example, in some embodiments sequence determination may be effected by identifying the ordering and locations of a single type of nucleotide, e.g. cytosines, within the target polynucleotide "CATCGC . . ." so that its sequence is represented as a binary code, e.g. "100101 . . ." for "C-(not C)-(not C)-C-(not C)-C . . ." and the like.

As used herein, the term "complexity" in reference to a population of polynucleotides means the number of different species of molecule present in the population.

DETAILED DESCRIPTION OF THE INVENTION

The invention involves the ligation of encoded adaptors specifically hybridized to the terminus or termini of one or more target polynucleotides. Sequence information about the region where specific hybridization occurs is obtained by "decoding" the oligonucleotide tags of the encoded adaptors thus ligated. In one aspect of the invention, multiple sets of encoded adaptors are ligated to a target polynucleotide at staggered cleavage points so that the encoded adaptors provide sequence information from each of a plurality of portions of the target polynucleotide. Such portions may be disjoint, overlapping or contiguous; however, preferably, the portions are contiguous and together permit the identification of a sequence of nucleotides equal to the sum of the lengths of the individual portions. In this aspect, there is only a single ligation of encoded adaptors followed by identification by "de-coding" the tags of the ligated adaptors. In another aspect of the invention, encoded adaptors are employed as an identification step in a process involving repeated cycles of ligation, identification, and cleavage, described more fully below.

In the latter embodiment, the invention makes use of nucleases whose recognition sites are separate from their cleavage sites. Preferably, such nucleases are type IIs restriction endonucleases. The nucleases are used to generate protruding strands on target polynucleotides to which encoded adaptors are ligated. The amount of sequence information obtained in a given embodiment of the invention depends in part on how many such nucleases are employed and the length of the protruding strand produce upon cleavage.

An important aspect of the invention is the capability of sequencing many target polynucleotides in parallel. In this aspect, the method of the invention comprises the following steps: (a) attaching a first oligonucleotide tag from a repertoire of tags to each polynucleotide in a population of polynucleotides such that each first oligonucleotide tag from the repertoire is selected from a first minimally cross-hybridizing set; (b) sampling the population of polynucleotides such that substantially all different polynucleotides in the population have different first oligonucleotide tags attached; (c) ligating one or more encoded adaptors to an end of each of the polynucleotides in the population, each encoded adaptor having a second oligonucleotide tag selected from a second minimally cross-hybridizing set and a protruding strand complementary to a protruding strand of a polynucleotide of the population; (d) sorting the polynucleotides of the population by specifically hybridizing the first oligonucleotide tags with their respective complements, the respective complements being attached as uniform populations of substantially identical oligonucleotides in spatially discrete regions on the one or more solid phase supports; and (e) identifying one or more nucleotides in said protruding strands of the polynucleotides by specifically hybridizing a tag complement to each second oligonucleotide tag of the one or more encoded adaptors. In this embodiment, the one or more encoded adaptors may be ligated to an end of the polynucleotides either before or after the polynucleotides have been sorted onto solid phase supports by the first oligonucleotide tags. In the preferred embodiment, encoded adaptors include a type IIs restriction endonuclease site which permits the encoded adaptors to be cleaved from the polynucleotides and the polynucleotides shortened after sequence identification.

In accordance with the preferred embodiment, the method further includes repeated cycles of ligation, identification, and cleavage, such that one or more nucleotides are identified in each cycle. Preferably, from 2 to 6 nucleotides are identified and their ordering determined in each cycle.

Sequence Analysis without Cycles of Ligation and Cleavage

Sequence analysis without cycles of ligation and cleavage in accordance with the invention is illustrated by the embodiment of FIGS. 1a through 1e. In this embodiment, k target polynucleotides are prepared as described below, and in Brenner, International patent applications PCT/US95/12791 and PCT/US96/09513. That is, a sample is taken from a population of polynucleotides conjugated with oligonucleotide tags designated by small "t's." These tags are sometimes referred to as oligonucleotide tagS for storing, or as "first" oligonucleotide tags. The tag-polynucleotide conjugates of the sample are amplified, e.g. by polymerase chain reaction (PCR) or by cloning, to give 1 through k populations of conjugates, indicated by (14)–(18) in FIG. 1a. Preferably, the ends of the conjugates opposite of the (small "t") tags are prepared for ligating one or more adaptors, each of which contains a recognition site for a nuclease whose cleavage site is separate from its recognition site. In the illustrated embodiment, three such adaptors, referred to herein as "cleavage adaptors," are employed. The number of such adaptors employed depends on several factors, including the amount of sequence information desired, the availability of type IIs nucleases with suitable reaches and cleavage characteristics, and the like. Preferably, from one to three cleavage adaptors are used, and the adaptors are design to accommodate different type IIs nucleases capable of generating at least four-nucleotide protruding strands after cleavage.

If the method of the invention is being applied to signature sequencing of a cDNA population, then prior to ligation of the cleavage adaptors, the tag-polynucleotide conjugates may be cleaved with a restriction endonuclease with a high frequency of recognition sites, such as Taq I, Alu I, HinP1 I, Dpn II, Nla III, or the like. For enzymes, such as Alu I, that leave blunt ends, a staggered end may be produced with T4 DNA polymerase, e.g. as described in Brenner, International patent application PCT/US95/12791, and Kuijper et al, Gene, 112: 147–155 (1992). If the target polynucleotides are prepared by cleavage with Taq I, then the following ends are available for ligation:

```
        cgannnn . . . -3'
          tnnnn . . . -5'
```

Thus, an exemplary set of three cleavage adaptors may be constructed as follows:

```
(1) NN . . . NGAAGA      cgannnnnnnnnnnnnnnnnnn . . . -3'
    NN . . . NCTTTCTGCp  tnnnnnnnnnnnnnnnnnnnnn . . . -5'

(2) NN . . . NGCAGCA     cgannnnnnnnnnnnnnnnnnn . . . -3'
    NN . . . NCGTCGTTGCp tnnnnnnnnnnnnnnnnnnnnn . . . -5'

(3) NN . . . NGGGA       cgannnnnnnnnnnnnnnnnnn . . . -3'
    NN . . . NCCCTGCp    tnnnnnnnnnnnnnnnnnnnnn . . . -5'
``` where cleavage adaptors (1),(2), and (3) are shown in capital letters with the respective recognition sites of nucleases Bbs I, Bbv I, and Bsm FI underlined and a 5' phosphate indicated as "p." The double underlined portions of the target polynucleotide indicate the positions of the protruding strands after ligation and cleavage. In all cases, the target polynucleotide is left with a 5' protruding strand of four nucleotides. Clearly, many different embodiments can be constructed using different numbers and kinds of nucleases. As discussed in Brenner, U.S. Pat. No. 5,599,675, preferably prior to cleavage, internal Bbs I, Bbv I, and Bsm FI sites are blocked, e.g. by methylation, to prevent undesirable cleavages at internal sites of the target polynucleotide.

Figure 1B:
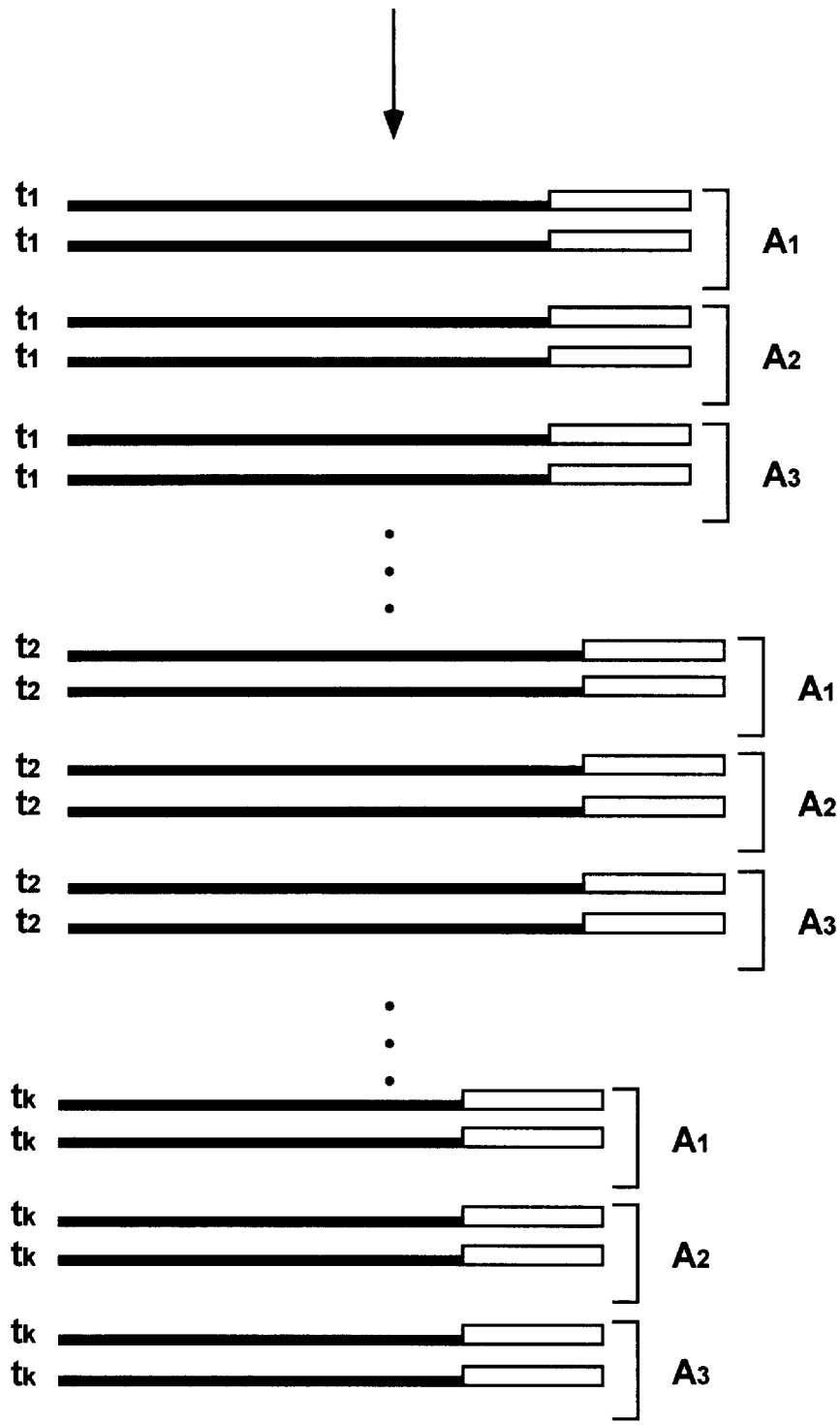
Figure 1C:
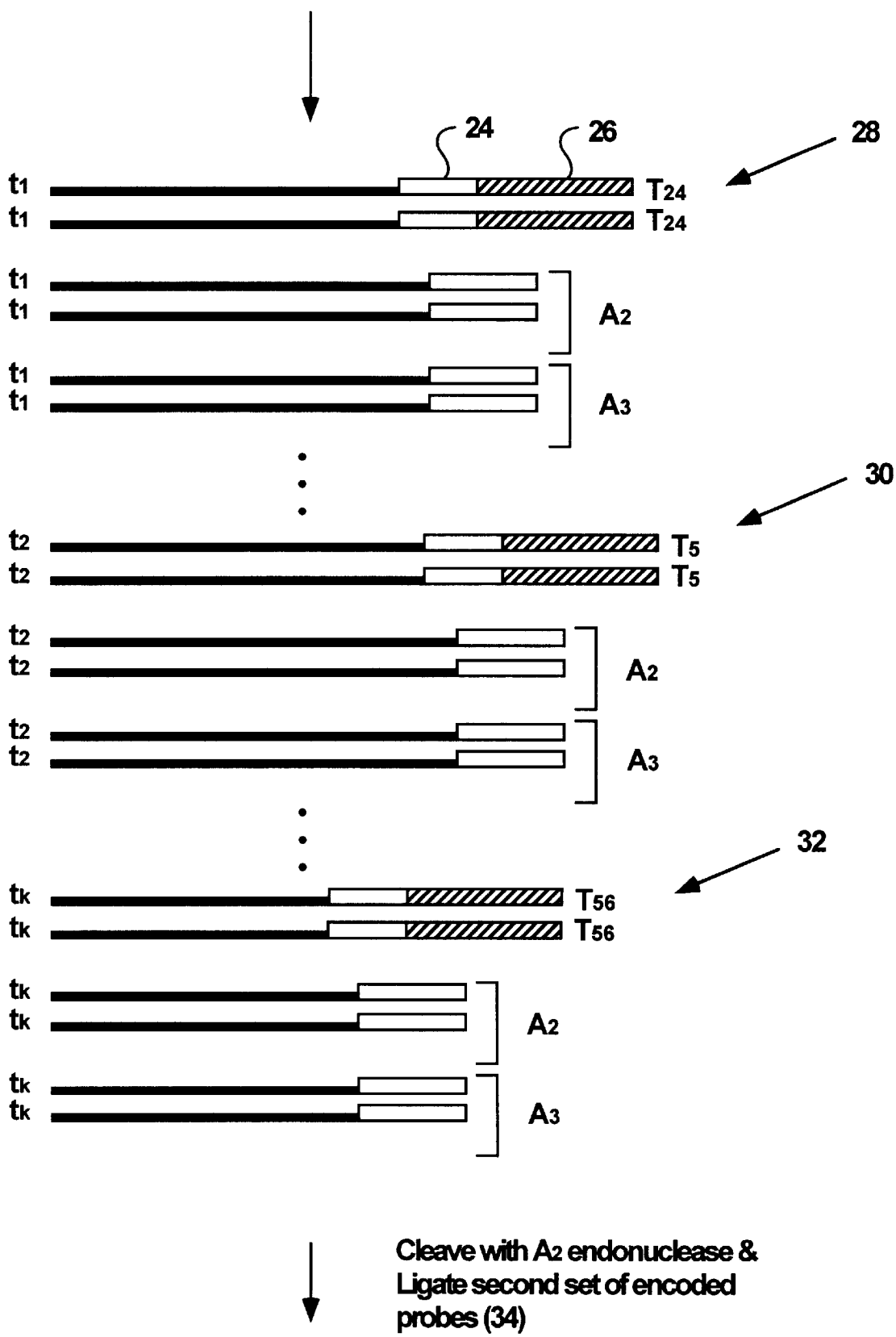
Figure 1D:
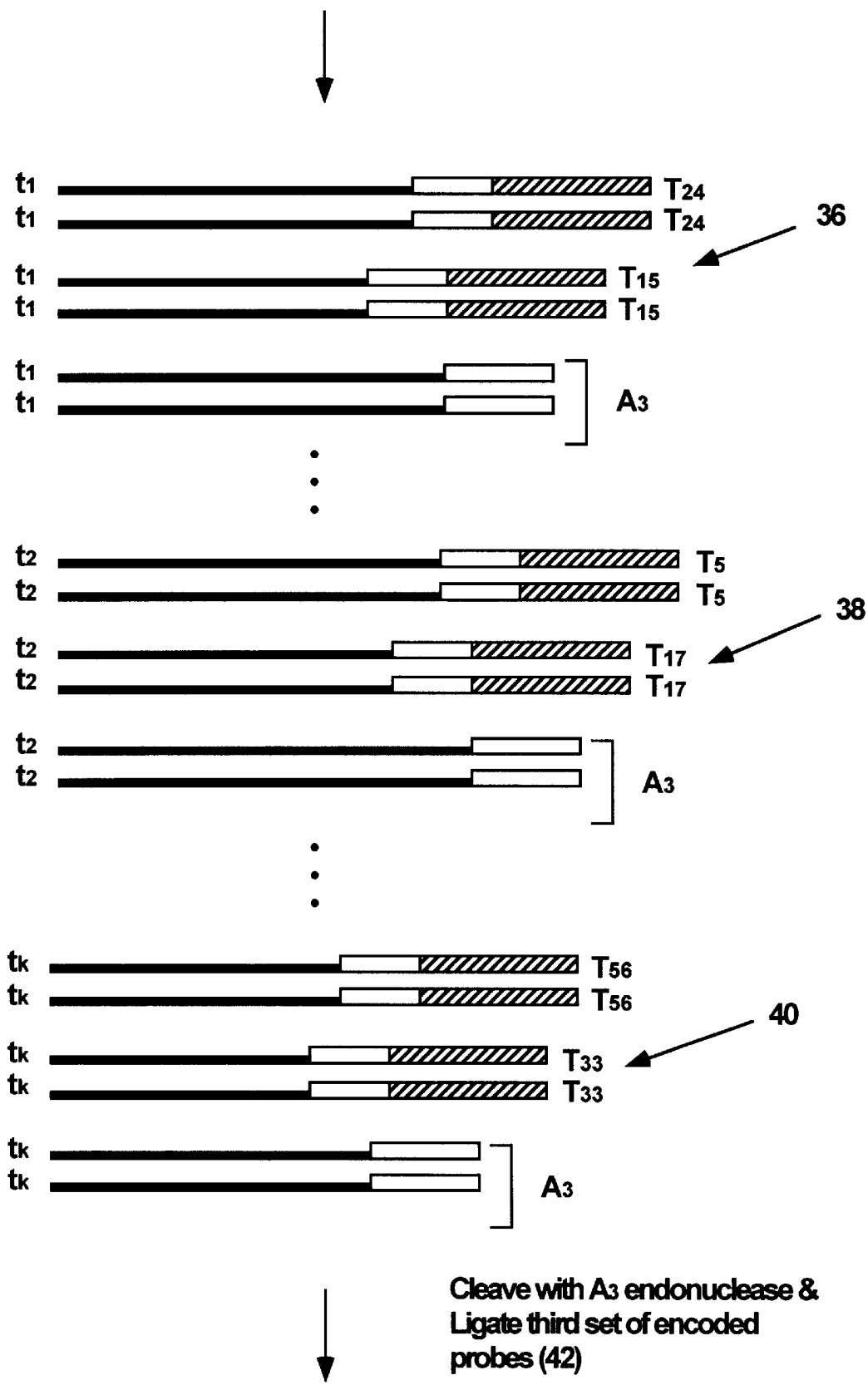
Figure 1E:
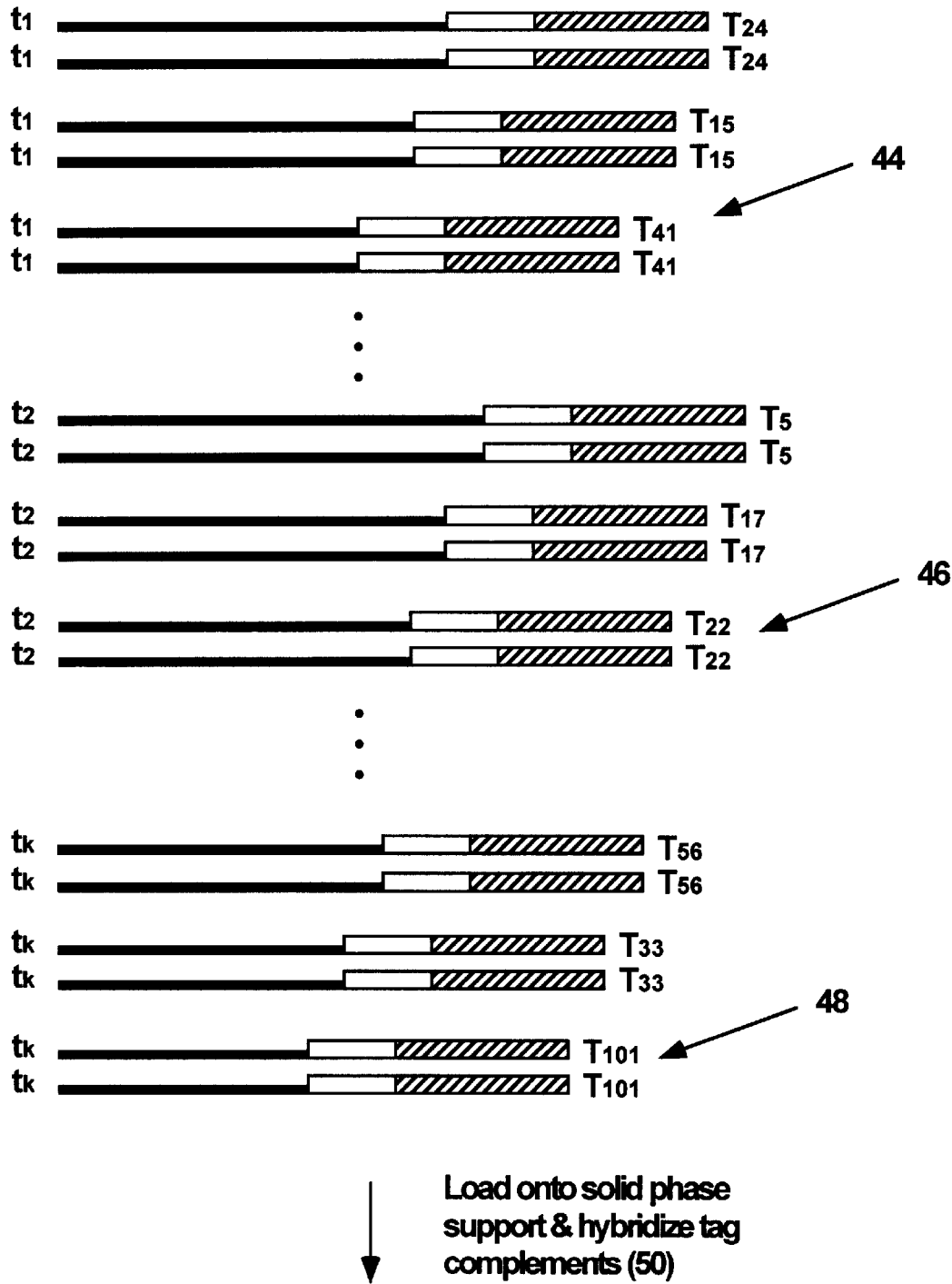

Returning to the illustrated embodiment, cleavage adaptors $A_1$, $A_2$, $A_3$ are ligated (20) in a concentration ratio of 1:1:1 to the k target polynucleotides to give the conjugates shown in FIG. 1b, such that within each population of tag-polynucleotide conjugates there are approximately equal numbers of conjugates having $A_1$,$A_2$, and $A_3$ attached. After ligation (20), the target polynucleotides are successively cleaved with each of the nucleases of the cleavage adaptors and ligated to a set of encoded adaptors. First, the target polynucleotides are cleaved (22) with the nuclease of cleavage adaptor $A_1$ after which a first set of encoded adaptors are ligated to the resulting protruding strands. The cleavage results in about a third of the target polynucleotides of each type, i.e. $t_1$, $t_2$, . . . $t_k$, being available for ligation. Preferably, the encoded adaptors are applied as one or more mixtures of adaptors which taken together contain every possible sequence of a protruding strand. Reaction conditions are selected so that only encoded adaptors whose protruding strands form perfectly matched duplexes with those of the target polynucleotide are ligated to form encoded conjugates (28), (30), and (32). The capital "T"s with subscripts indicate that unique oligonucleotide tags are carried by the encoded adaptors for labeling. The oligonucleotide tags carried by encoded adaptors are sometimes referred to tags for delivering labels to the encoded adaptors, or as "second" oligonucleotide tags. As described more fully below, single stranded oligonucleotide tags used for sorting preferably consists of only three of the four nucleotides, so that a T4 DNA polymerase "stripping" reaction, e.g. Kuijper et al (cited above), can be used to prepare target polynucleotides for loading onto solid phase supports. On the other hand, oligonucleotide tags employed for delivering labels may consist of all for nucleotides.

As mentioned above, encoded adaptors comprise a protruding strand (24) and an oligonucleotide tag (26). Thus, if the "$A_1$" cleavage of the $t_1$-polynucleotide conjugates results in the following ends:

```
5'- . . . nnnnnnnnn
3'- . . . nnnnnnnnnacct
``` then oligonucleotide tag $T_{24}$ could have the following structure (SEQ ID NO: 1):

```
tggattctagagagagagagagagag -3'
   aagatctctctctctctctctctc
``` where the double stranded portion may be one of a set of 48(=12 nucleotide positions×4 kinds of nucleotide) double stranded 20-mer oligonucleotide tags that forms a perfectly matched triplex with a unique tag complement and forms a triplex with at least 6 mismatches with all other tag complements. The encoded adaptors in this example may be ligated to the target polynucleotides in one or more mixtures of a total of 768 (3×256) members. Optionally, an encoded adaptor may also comprise a spacer region, as shown in the above example where the 4 nucleotide sequence "ttct" serves as a spacer between the protruding strand and the oligonucleotide tag.

After ligation of the first set of encoded adaptors (28), (30), and (32), the tag-polynucleotide conjugates are cleaved (34) with the nuclease of cleavage adaptor $A_2$, after which a second set of encoded adaptors is applied to form conjugates (36), (38), and (40). Finally, the tag-polynucleotide conjugates are cleaved (42) with the nuclease of cleavage adaptor $A_3$, after which a third set of encoded adaptors is applied to form conjugates (44), (46), and (48). After completion of the succession of cleavages and ligations of encoded adaptors, the mixture is loaded (50) onto one or more solid phase supports via oligonucleotide tags $t_1$ through $t_k$ as described more fully below, and as taught by Brenner, e.g. PCT/US95/12791 or PCT/US96/09513. If a single target polynucleotide were being analyzed, then clearly multiple oligonucleotide tags, $t_1$, $t_2$, . . . $t_k$, would not be necessary. In such an embodiment, biotin, or like moiety, could be employed to anchor the polynucleotide-encoded adaptor conjugate, as no sorting would be required. Also, the ordering of the steps of cleavage, ligation, and loading onto solid phase supports depends on the particular embodiment implemented. For example, the tag-polynucleotide conjugates may be loaded onto solid phase support first, followed by ligation of cleavage adaptors, cleavage thereof, and ligation of encoded adaptors; or, the cleavage adaptors may be ligated first, followed by loading, cleavage, and ligation of encoded adaptors; and so on.

After encoded adaptors are ligated to the ends of a target polynucleotide in accordance with the invention, sequence information is obtained by successively applying labeled tag complements, either individually or as mixtures under conditions that permit the formation of perfectly matched duplexes and/or triplexes between the oligonucleotide tags of the encoded adaptors and their respective tag complements. The numbers and complexity of the mixtures depends on several factors, including the type of labeling system used, the length of the portions whose sequences are to be identified, whether complexity reducing analogs are used, and the like. Preferably, for the embodiment illustrate in FIGS. 1a through 1e, a single fluorescent dye is used to label each of 48(=3×16) tag complements. The tag complements are applied individually to identify the nucleotides of each of the four-nucleotide portions of the target polynucleotide (i.e., 4 tag complements for each of 12 positions for a total of 48). Clearly, portions of different lengths would require different numbers of tag complements, e.g. in accordance with this embodiment, a 5-nucleotide portion would require 20 tag complements, a 2-nucleotide portion would require 8 tag complements, and so on. The tag complements are applied under conditions sufficiently stringent so that only perfectly match duplexes are formed, signals from the fluorescent labels on the specifically hybridizing tag complements are measured, and the tag complements are washed from the encoded tags so that the next mixture can be applied. The 16 tag complements have a one-to-one correspondence with the following sequences of the 4-mer portions of the target sequence:

| ANNN | NANN | NNAN | NNNA |
|------|------|------|------|
| CNNN | NCNN | NNCN | NNNC |
| GNNN | NGNN | NNGN | NNNG |
| TNNN | NTNN | NNTN | NNNT | where "N" is any one of the nucleotides, A, C, G, or T. Thus, for each nucleotide position four separate interrogations are made, one for each kind of nucleotide. This embodiment incorporates a significant degree of redundancy (a total of 16 tag complements are used to identify 4 nucleotide) in exchange for increased reliability of nucleotide determination.

Alternatively, 12 mixtures of 4 tag complements each could applied in succession by using four spectrally distinguishable fluorescent dyes, such that there is a one-to-one correspondence between dyes and kinds of nucleotide. For example, a mixture of 4 tag complements may identify nucleotide "x" in the protruding strand sequence "nnxn" so that a first fluorescent label is observed is x=A, a second fluorescent label is observed if x=C, a third fluorescent label is observed if x=G, and so on.

Further sequence information can be obtained using a embodiment described above in a process analogous to the "multi-stepping" process disclosed in Brenner, International patent application PCT/US95/03678. In this embodiment, a fourth adaptor, referred to herein as a "stepping adaptor," is ligated to the ends of the target polynucleotides along with cleavage adaptors $A_1$, $A_2$, and $A_3$, for example, in a concentration ratio of 3:1:1:1. Thus, approximately half of the available ends are ligated to the stepping adaptor. The stepping adaptor includes a recognition site for a type IIs nuclease positioned such that its reach (defined below) will permit cleavage of the target polynucleotides at the end of the sequence determined via cleavage adaptors $A_1$, $A_2$, and $A_3$. an example of a stepping adaptor that could be used with the above set of cleavage adaptors is as follows:

```
NN . . . NCTGGAGA        cgannnnnnnnnnnnnnnnnnnn . . . -3'
NN . . . NGACCTCTGCp     tnnnnnnnnnnnnnnnnnnnnn . . . -5'
``` where, as above, the recognition site of the nuclease, in this case BpM I, is singly underlined and the nucleotides at the cleavage site are doubly underlined. The target polynucleotides cleaved with the nuclease of the stepping adaptor may be ligated to a further set of cleavage adaptors $A_4$, $A_5$, and $A_6$, which may contain nuclease recognition sites that are the same or different than those contained in cleavage adaptors $A_1$, $A_2$, and $A_3$. Whether or not an enlarged set of encoded adaptors is required depends on whether cleavage and ligation reactions can be tolerated in the signal measurement apparatus. If, as above, it is desired to minimize enzyme reactions in connection with signal measurement, then additional sets of encoded adaptors must be employed. That is, where above 768 oligonucleotide tags and tag complements were called for, with six cleavage reactions producing protruding strands of four nucleotides each, 1536 oligonucleotide tags and tag complements (24 mixtures of 64 tag complements each) would be required. Exemplary, cleavage adaptors $A_4$, $A_5$, and $A_6$, with the same nuclease recognition sites as $A_1$, $A_2$, and $A_3$, and which could be used with the stepping adaptor shown above are as follows:

```
(4) NN . . . NGAAGACNN      nnnnnnnnnnnnnnnnnn . . . -3'
    NN . . . NCTTCTGp       nnnnnnnnnnnnnnnnnn . . . -5'

(5) NN . . . NGCAGCACNN     nnnnnnnnnnnnnnnnnn . . . -3'
    NN . . . NCGTCGTGp      nnnnnnnnnnnnnnnnnn . . . -5'

(6) NN . . . NGGGACNN       nnnnnnnnnnnnnnnnnn . . . -3'
    NN . . . NCCCTGp        nnnnnnnnnnnnnnnnnn . . . -5'
``` where the cleavage sites are indicated by double underlining. Cleavage adaptors $A_4$, $A_5$, and $A_6$ are preferably applied as mixtures, such that every possible two-nucleotide protruding strand is represented.

Once the encoded adaptors have been ligated, the target polynucleotides are prepared for loading onto solid phase supports, preferably microparticles, as disclosed in Brenner, International patent application PCT/US95/12791. Briefly, the oligonucleotide tags for sorting are rendered single stranded using a "stripping" reaction with T4 DNA polymerase, e.g. Kuijper et al (cited above). The single stranded oligonucleotide tags are specifically hybridized and ligated to their tag complements on microparticles. The loaded microparticles are then analyzed in an instrument, such as described in Brenner (cited above) which permits the sequential deliver, specific hybridization, the removal of labeled tag complements to encoded adaptors.

In embodiments where encoded adaptors are ligated to a target polynucleotide (or population of target polynucleotides) only one time, there are several non-enzymatic template-driven methods of ligation that may used in accordance with the invention. Such ligation methods include, but are not limited to, those disclosed in Shabarova, Biochimie 70: 1323–1334 (1988); Dolinnaya et al, Nucleic Acids Research, 16: 3721–3738 (1988); Letsinger et al, U.S. Pat. No. 5,476,930; Gryaznov et al, Nucleic Acids Research, 22: 2366–2369 (1994); Kang et al, Nucleic Acids Research, 23: 2344–2345 (1995); Gryaznov et al, Nucleic Acids Research, 21: 1403–1408 (1993); Gryaznov, U.S. Pat. No. 5,571,677; and like references. Preferably, non-enzymatic ligation is carried out by the method of Letsinger et al (cited above). In this method, an encoded adaptor having a 3'-bromoacetylated end is reacted with a polynucleotide having a complementary protruding strand and a thiophosphoryl group at its 5' end. An exemplary encoded adaptor employing such chemistry has the following structure:

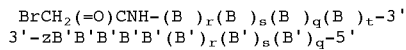

where B and B' are nucleotides and their complements, and z, r, s, q, and t are as described below. Br, C, H, and N have their usual chemical meanings. As explained in the above references, in a template-driven reaction, the 3'-bromacetylated oligonucleotide reacts spontaneously with an oligonucleotide having a 5'-thiophosphoryl group under aqueous conditions to form a thiophosphorylacetylamino linkage. A thiophosphoryal group is readily attached to the 5' hydroxy of a target polynucleotide by treatment with T4 kinase in the presence of adenosine-5'-O-(1-thiotriphosphate), i.e. γ-S-ATP, as described in Kang et al (cited above).

Sequence Analysis with Cycles of Ligation and Cleavage

Encoded adaptors may be used in an adaptor-based method of DNA sequencing that includes repeated cycles of ligation, identification, and cleavage, such as the method described in Breenner, U.S. Pat. No. 5,599,675. Briefly, such a method comprises the following steps: (a) ligating an encoded adaptor to an end of a polynucleotide, the encoded adaptor having a nuclease recognition site of a nuclease whose cleavage site is separate from its recognition site; (b) identifying one or more nucleotides at the end of the polynucleotide by the identity of the encoded adaptor ligated thereof; (c) cleaving the polynucleotide with a nuclease recognizing the nuclease recognition site of the encoded adaptor such that the polynucleotide is shortened by one or more nucleotides; and (d) repeating said steps (a) through (c) until said nucleotide sequence of the polynucleotide is determined. In the identification step, successive sets of tag complements are specifically hybridized to the respective tags carried by encoded adaptors ligated to the ends of the target polynucleotides, as described above. The type and sequence of nucleotides in the protruding strands of the polynucleotides are identified by the label carried by the specifically hybridized tag complement and the set from which the tag complement came, as described above.

Oligonucleotide Tags and Tag Complements

Oligonucleotide tags are employed for two different purposes in the preferred embodiments of the invention: Oligonucleotide tags are employed as described in Brenner, International patent applications PCT/US95/12791 and PCT/US96/09513, to sort large numbers of polynucleotides, e.g. several thousand to several hundred thousand, from a mixture into uniform populations of identical polynucleotides for analysis, and they are employed to deliver labels to encoded adaptors that number in the range of a few tens to a few thousand. For the former use, large numbers, or repertoires, of tags are typically required, and therefore synthesis of individual oligonucleotide tags is problematic. In these embodiments, combinatorial synthesis of the tags is preferred. On the other hand, where extremely large repertoires of tags are not required—such as for delivering labels to encoded adaptors, oligonucleotides tags of a minimally cross-hybridizing set may be separately synthesized, as well as synthesized combinatorially.

As described in Brenner (cited above), the nucleotide sequence of oligonucleotides of a minimally cross-hybridizing set of conveniently enumerated by simple computer programs, such as those exemplified by the programs whose source codes are listed in Appendices I and II. Similar computer programs are readily written for listing oligonucleotides of minimally cross-hybridizing sets of any embodiment of the invention. Table I below provides guidance as to the size of sets of minimally cross-hybridizing oligonucleotides for the indicated lengths and number of nucleotides differences. The above computer programs were used to generate the numbers.

TABLE I

Minimally Cross-Hybridizing Sets of Words Consisting of Four Nucleotides

| Oligonucleotide Word Length | Nucleotide Difference between Oligonucleotides of Minimally Cross-Hybridizing Set | Maximal Size of Minimally Cross-Hybridizing Set | Size of Repertoire with Three Words | Size of Repertoire with Four Words |
|---|---|---|---|---|
| 4 | 3 | 11 | 1331 | 14,641 |
| 6 | 4 | 25 | 15,625 | $3.9 \times 10^5$ |
| 6 | 5 | 4 | 64 | 256 |
| 8 | 4 | 225 | $1.14 \times 10^7$ | |
| 8 | 5 | 56 | $1.75 \times 10^5$ | |
| 8 | 6 | 17 | 4913 | |
| 12 | 8 | 62 | | |

Sets containing several hundred to several thousands, or even several tens of thousands, of oligonucleotides may be synthesized directly by a variety of parallel synthesis approaches, e.g. as disclosed in Frank et al, U.S. Pat. No. 4,689,405; Frank et al, Nucleic Acids Research, 11: 4365–4377 (1983); Matson et al, Anal. Biochem., 224: 110–116 (1995); Fodor et al, International application PCT/US93/04145; Pease et al, Proc. Natl. Acad. Sci., 91: 5022–5026 (1994); Southern et al, J. Biotechnology, 35: 217–227 (1994), Brennan, International application PCT/US94/05896; Lashkari et al, Proc. Natl. Acad. Sci., 92: 7912–7915 (1995); or the like.

Preferably, tag complements in mixtures, whether synthesized combinatorially or individually, are selected to have similar duplex or triplex stabilities to one another so that perfectly matched hybrids have similar or substantially identical melting temperatures. This permits mis-matched tag complements to be more readily distinguished from perfectly matched tag complements when applied to encoded adaptors, e.g. by washing under stringent conditions. For combinatorially synthesized tag complements, minimally cross-hybridizing sets may be constructed from subunits that make approximately equivalent contributions to duplex stability as every other subunit in the set. Guidance for carrying out such selections is provided by published techniques for selecting optimal PCR primers and calculating duplex stabilities, e.g. Rychlik et al, Nucleic Acids Research, 17: 8543–8551 (1989) and 18: 6409–6412 (1990); Breslauer et al, Proc. Natl. Acad. Sci., 83: 3746–3750 (1986); Wetmur, Crit. Rev. Biochem. Mol. Bio., 26: 227–259 (1991); and the like. When smaller numbers of oligonucleotide tags are required, such as for delivering labels to encoded adaptors, the computer programs of Appendices I and II may be used to generate and list the sequences of minimally cross-hybridizing sets of oligonucleotides that are used directly (i.e. without concatenation into "sentences"). Such lists can be further screened for additional criteria, such as GC-content, distribution of mismatches, theoretical melting temperature, and the like, to form additional minimally cross-hybridizing sets.

For shorter tags, e.g. about 30 nucleotides or less, the algorithm described by Rychlik and Wetmur is preferred for calculating deplex stability, and for longer tags, e.g. about 30–35 nucleotides or greater, an algorithm disclosed by Suggs et al, pages 683–693 in Brown, editor, ICN-UCLA Symp. Dev. Biol., Vol. 23 (Academic Press, New York, 1981) may be conveniently employed. Clearly, there are many approaches available to one skilled in the art for designing sets of minimally cross-hybridizing subunits within the scope of the invention. For example, to minimize the affects of different base-stacking energies of terminal nucleotides when subunits are assembled, subunits may be provided that have the same terminal nucleotides. In this way, when subunits are linked, the sum of the base-stacking energies of all the adjoining terminal nucleotides will be the same, thereby reducing or eliminating variability in tag melting temperatures.

In multi-subunit tags, a "word" of terminal nucleotides, shown in italic below, may also be added to each end of a tag so that a perfect match is always formed between it and a similar terminal "work" on any other tag complement. Such an augmented tag would have the form:

| W  | $W_1$  | $W_2$  | ... | $W_{k-1}$  | $W_k$  | W  |
|----|--------|--------|-----|------------|--------|----|
| W' | $W_1'$ | $W_2'$ | ... | $W_{k-1}'$ | $W_k'$ | W' | where the primed W's indicate complements. With ends of tags always forming perfectly matched duplexes, all mismatched words will be internal mismatches thereby reducing the stability of tag-complement duplexes that otherwise would have mismatched words at their ends. It is well known that duplexes with internal mismatches are significantly less stable than duplexes with the same mismatch at a terminus.

With oligonucleotide tags used for sorting, a preferred embodiment of minimally cross-hybridizing sets are those whose subunits are made up of three of the four natural nucleotides. As will be discussed more sully below, the absence of one type of nucleotide in the oligonucleotide tags permits target polynucleotides to be loaded onto solid phase supports by use of the 5'→3' exonuclease activity of a DNA polymerase. The following is an exemplary minimally cross-hybridizing set of subunits each comprising four nucleotides selected from the group consisting of A, G, and T;

TABLE II

| Word:     | $w_1$ | $w_2$ | $w_3$ | $w_4$ |
|-----------|-------|-------|-------|-------|
| Sequence: | GATT  | TGAT  | TAGA  | TTTG  |
| Word:     | $w_5$ | $w_6$ | $w_7$ | $w_8$ |
| Sequence: | GTAA  | AGTA  | ATGT  | AAAG  |

In this set, each member would form a duplex having three mismatched bases with the complement of every other member.

With oligonucleotide tags used for delivering labels to encoded adaptors, all four nucleotides are employed.

The oligonucleotide tags of the invention and their complements are conveniently synthesized on an automated DNA synthesizer, e.g. an Applied Biosystems, Inc. (Foster City, Calif.) model 392 or 394 DNA/RNA Synthesizer, using standard chemistries, such as phosphoramidite chemistry, e.g. disclosed in the following references: Beaucage and Iyer, Tetrahedron, 48: 2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. Alternative chemistries e.g. resulting in non-natural backbone groups, such as peptide nucleic acids (PNAs), N3'→P5' phosphoramidates, and the like, may also be employed. In some embodiments, tags may comprise naturally occurring nucleotides that permit processing or manipulation by enzymes, while the corresponding tag complements may comprise non-natural nucleotide analogs, such as peptide nucleic acids, or like compounds, that promote the formation of more stable duplexes during sorting. In the case of tags used for delivering label to encoded adaptors both the oligonucleotide tags and tag complements may be constructed from non-natural nucleotides, or analogs, provided ligation can take place, either chemically or enigmatically.

Double stranded forms of tags may be made by separately synthesizing the complementary strands followed by mixing under conditions that permit duplex formation. Alternatively, double stranded tags may be formed by first synthesizing a single stranded repertoire linked to a known oligonucleotide sequence that serves as a primer binding site. The second strand is then synthesized by combining the single stranded repertoire with a primer and extending with a polymerase. This latter approach is described in Oliphant et al, Gene, 44: 177–183 (1986). Such duplex tags may then be inserted into cloning vectors along with target polynucleotides for storing and manipulation of the target polynucleotide in accordance with the invention.

When tag complements are employed that are made up of nucleotides that have enhanced binding characteristics, such as PNAs or oligonucleotide N3'→P5' phosphoramidates, sorting can be implemented through the formation of D-loops between tags comprising natural nucleotides and their PNA or phosphoramidate complements, as an alternative to the "stripping" reaction employing the 3'→5' exonuclease activity of a DNA polymerase to render a tag single stranded.

Oligonucleotide tags for storing may range in length from 12 to 60 nucleotides or basepairs. Preferably, oligonucleotide tags range in length from 18 to 40 nucleotides or basepairs. More preferably, oligonucleotide tags range in length from 25 to 40 nucleotides or basepairs. In terms of preferred and more preferred numbers of subunits, these ranges may be expressed as follows:

TABLE III

Numbers of Subunits in Tags in Preferred Embodiments

| Monomers in Subunit | Nucleotides in Oligonucleotide Tag | | |
|---|---|---|---|
| | (12–60) | (18–40) | (25–40) |
| 3 | 4–20 subunits | 6–13 subunits | 8–13 subunits |
| 4 | 3–15 subunits | 4–10 subunits | 6–10 subunits |
| 5 | 2–12 subunits | 3–8 subunits | 5–8 subunits |
| 6 | 2–10 subunits | 3–6 subunits | 4–6 subunits |

Most preferably, oligonucleotide tags for sorting are single stranded and specific hybridization occurs via Watson-Crick pairing with a tag complement.

Preferably, repertoires of single stranded oligonucleotide tags for sorting contain at least 100 members; more preferably, repertoires of such tags contain at least 1000 members; and most preferably, repertoires of such tags contain at least 10,000 members.

Preferably, repertoires of tag complements for delivering labels contain at least 16 members; more preferably, repertoires of such tags contain at least 64 members. Still more preferably, such repertoires of tag complements contain from 16 to 1024 members, e.g. a number for identifying nucleotides in protruding strands of from 2 to 5 nucleotides in length. Most preferably, such repertoires of tag complements contain from 64 to 256 members. Repertoires of desired sizes are selected by directly generating sets of words, or subunits, of the desired size, e.g. with the help of the computer programs of Appendices I and II, or repertoires are formed generating a set of words which are then used in a combinatorial synthesis scheme to give a repertoire of the desired size. Preferably, the length of single stranded tag complements for delivering labels is between 8 and 20. More preferably, the length is between 9 and 15.

Triplex Tags

In embodiments where specific hybridization occurs via triplex formation, coding of tag sequences follows the same principles as for duplex-forming tags; however, there are further constraints on the selection of subunit sequences. Generally, third strand association via Hoogsteen type of binding is most stable along homopyrimidine-homopurine tracks in a double stranded target. Usually, base triplets form in T-A*T or C-G*C motifs (where "-" indicates Watson-Crick pairing and "*" indicates Hoogsteen type of binding); however, other motifs are also possible. For example, Hoogsteen base pairing permits parallel and antiparallel orientations between the third strand (the Hoogsteen strand) and the purine-rich strand of the duplex to which the third strand binds, depending on conditions and the composition of the strands. There is extensive guidance in the literature for selecting appropriate sequences, orientation, conditions, nucleoside type (e.g. whether ribose or deoxyribose nucleosides are employed), base modifications (e.g. methylated cytosine, and the like) in order to maximize, or otherwise regulate, triplex stability as desired in particular embodiments, e.g. Roberts et al, Proc. Natl. Acad. Sci., 88: 9397–9401 (1991); Roberts et al, Science, 258: 1463–1466 (1992); Roberts et al, Proc. Natl. Acad. Sci., 93: 4320–4325 (1996); Distefano et al, Proc. Natl. Acad. Sci., 90: 1179–1183 (1993); Mergny et al, Biochemistry, 30: 9791–9798 (1991); Cheng et al, J. Am. Chem. Soc., 114: 4465–4474 (1992); Beal and Dervan, Nucleic Acids Research, 20: 2773–2776 (1992); Beal and Dervan, J. Am. Chem. Soc., 114: 4976–4982 (1992); Giovannangeli et al, Proc. Natl. Acad. Sci., 89: 8631–8635 (1992); Moser and Dervan, Science, 238: 645–650 (1987); McShan et al, J. Biol. Chem., 267: 5712–5721 (1992); Yoon et al, Proc. Natl. Acad. Sci., 89: 3840–3844 (1992); Blume et al, Nucleic Acids Research, 20: 1777–1784 (1992); Thuong and Helene, Angew. Chem. Int. Ed. Engl. 32: 666–690 (1993); Escude et al, Proc. Natl. Acad. Sci., 93: 4365–4369 (1996); and the like. Conditions for annealing single-stranded or duplex tags to their single-stranded or duplex complements are well known, e.g. Ji et al, Anal. Chem. 65: 1323–1328 (1993); Cantor et al, U.S. Pat. No. 5,482,836; and the like. Use of triplex tags in sorting has the advantage of not requiring a "stripping" reaction with polymerase to expose the tag for annealing to its complement.

Preferably, oligonucleotide tags of the invention employing triplex hybridization are double stranded DNA and the corresponding tag complements are single stranded. More preferably, 5-methylcytosine is used in place of cytosine in the tag complements in order to broaden the range of pH stability of the triplex formed between a tag and its complement. Preferred conditions for forming triplexes are fully disclosed in the above reference. Briefly, hybridization takes place in concentrated salt solution, e.g. 1.0 M NaCl, 1.0 M potassium acetate, or the like, at pH below 5.5 (or 6.5 if 5-methylcytosine is employed). Hybridization temperature depends on the length and composition of the tag; however, for an 18–20-mer tag or longer, hybridization at room temperature is adequate. Washes may be conducted with less concentrated salt solution, e.g. 10 mM sodium acetate, 100 mM MgCl$_2$, pH 5.8, at room temperature. Tags may be eluted from their tag complements by incubation in a similar salt solution at pH 9.0.

Minimally cross-hybridizing sets of oligonucleotide tags that form triplexes may be generated by the computer program of Appendix II, or similar programs. An exemplary set of double stranded 8-mer words are listed below in capital letters with the corresponding complements in small letters. Each such word differs from each of the other words in the set by three base pairs.

TABLE IV
Exemplary Minimally Cross-Hybridizing
Set of DoubleStranded 8-mer Tags

| | | | |
|---|---|---|---|
| 5'-AAGGAGAG | 5'-AAAGGGGA | 5'-AGAGAAGA | 5'-AGGGGGGG |
| 3'-TTCCTCTC | 3'-TTTCCCCT | 3'-TCTCTTCT | 3'-TCCCCCCC |
| 3'-ttcctctc | 3'-tttcccct | 3'-tctcttct | 3'-tcccccc |
| 5'-AAAAAAAA | 5'-AAGAGAGA | 5'-AGGAAAAG | 5'-GAAAGGAG |
| 3'-TTTTTTTT | 3'-TTCTCTCT | 3'-TCCTTTTC | 3'-CTTTCCTC |
| 3'-tttttttt | 3'-ttctctct | 3'-tccttttc | 3'-ctttcctc |
| 5'-AAAAAGGG | 5'-AGAAGAGG | 5'-AGGAAGGA | 5'-GAAGAAGG |
| 3'-TTTTTCCC | 3'-TCTTCTCC | 3'-TCCTTCCT | 3'-CTTCTTCC |
| 3'-tttttccc | 3'-tcttctcc | 3'-tccttcct | 3'-cttcttcc |

TABLE IV-continued
Exemplary Minimally Cross-Hybridizing
Set of DoubleStranded 8-mer Tags

| | | | |
|---|---|---|---|
| 5'-AAAGGAAG | 5'-AGAAGGAA | 5'-AGGGGAAA | 5'-GAAGAGAA |
| 3'-TTTCCTTC | 3'-TCTTCCTT | 3'-TCCCCTTT | 3'-CTTCTCTT |
| 3'-tttccttc | 3'-tcttcctt | 3'-tccccttt | 3'-cttctctt |

TABLE V

Repertoire Size of Various Double Stranded Tags That Form Triplexes with Their Tag Complements

| Oligonucleotide Word Length | Nucleotide Difference between Oligonucleotides of Minimally Cross-Hybridizing Set | Maximal Size of Minimally Cross-Hybridizing Set | Size of Repertoire with Four Words | Size of Repertoire with Five Words |
|---|---|---|---|---|
| 4 | 2 | 8 | 4096 | $3.2 \times 10^4$ |
| 6 | 3 | 8 | 4096 | $3.2 \times 10^4$ |
| 8 | 3 | 16 | $6.5 \times 10^4$ | $1.05 \times 10^6$ |
| 10 | 5 | 8 | 4096 | |
| 15 | 5 | 92 | | |
| 20 | 6 | 768 | | |
| 20 | 7 | 484 | | |
| 20 | 8 | 189 | | |
| 20 | 9 | 30 | | |

Synthesis and Structure of Adaptors

The encoded adaptors and cleavage adaptors are conveniently synthesized on automated DNA synthesizers using stranded chemistries, such as phosphoramidite chemistry, e.g. disclosed in the following reference: Beaucage and Iyer, Tetrahedron, 48: 2223–2311 (1992); Molko et al, U.S. Pat. No. 4,980,460; Koster et al, U.S. Pat. No. 4,725,677; Caruthers et al, U.S. Pat. Nos. 4,415,732; 4,458,066; and 4,973,679; and the like. Alternative chemistries, e.g. resulting in non-natural backbone groups, such as phosphorothioate, phosphoramidate, and the like, may also be employed provided that the resulting oligonucleotides are compatible with the ligation and/or cleavage reagents used in a particular embodiment. Typically, after synthesis of complementary strands, the strands are combined to form a double stranded adaptor. The protruding strand of an encoded adaptor may be synthesized as a mixture, such that every possible sequence is represented in the protruding portion. Such mixtures are readily synthesized using well known techniques, e.g. as disclosed in Telenius et al, Genomics, 13: 718–725 (1992); Welsh et al, Nucleic Acids Research, 19: 5275–5279 (1991); Grothues et al, Nucleic Acids Research, 21: 1321–1322 (1993); Hartley, European patent application 90304496.4; and the like. Generally, these techniques simply call for the application of mixtures of the activated monomers to the growing oligonucleotide during the coupling steps where one desires to introduce multiple nucleotides. As discussed above, in some embodiments it may be desirable to reduce the complexity of the adaptors. This can be accomplished using complexity reducing analogs, such as deoxyinosine, 2-aminopurine, or the like, e.g. as taught in Kong Thoo Lin et al, Nucleic Acids Research, 20: 5149–5152, or by U.S. Pat. No. 5,002,867; Nichols et al, Nature, 369: 492–493 (1994); and the like.

In some embodiments, it may be desirable to synthesize encoded adaptors or cleavage adaptors as a single polynucleotide which contains self-complementary regions. After synthesis, the self-complementary regions are allowed to anal to form a adaptor with a protruding strand at one end and a single stranded loop at the other end. Preferably, in such embodiments the loop region may comprise from about 3 to 10 nucleotides, or other comparable linking moieties, e.g. alkylether groups, such as disclosed in U.S. Pat. No. 4,914,210. Many techniques are available for attaching reactive groups to the bases or internucleoside linkages for labeling, as discussed in the references cited below.

When conventional ligases are employed in the invention, as described more fully below, the 5' end of the adaptor may be phosphorylated in some embodiments. A 5' monophosphate can be attached to a second oligonucleotide either chemically or enzymatically with a kinase, e.g. Sambrook et al, Molecular Cloning: a Laboratory Manual, 2nd Edition (Cold Spring Harbor Laboratory, New York, 1989). Chemical phosphorylation is described by Horn and Urdea, Tetrahedron Lett., 27: 4705 (1986), and reagents for carrying out the disclosed protocols are commercially available, e.g. 5' Phosphate-ON™ from Clontech Laboratories (Palo Alto, Calif.).

Encoded adaptors of the invention can have several embodiments depending, for example, on whether single or double stranded tags are used, whether multiple tags are used, whether a 5' protruding strand or 3' protruding strand is employed, whether a 3' blocking group is used, and the like. Formulas for several embodiments of encoded adaptors are shown below. Preferred structures for encoded adaptors using one single stranded tag are as follows:

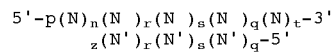

or

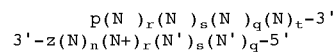

where N is a nucleotide and N' is its complement, p is a phosphate group, z is a 3' hydroxyl or a 3' blocking group, n is an integer between 2 and 6, inclusive, r is an integer greater than or equal to 0, s is an integer which is either between four and six whenever the encoded adaptor has a nuclease recognition site or is 0 whenever there is no nuclease recognition site, q is an integer greater than or equal to 0, and t is an integer between 8 and 20, inclusive. More preferably, n is 4 or 5, and t is between 9 and 15, inclusive. Whenever an encoded adaptor contains a nuclease recognition site, the region of "r" nucleotide pairs is selected so that a predetermined number of nucleotides are cleaved from a target polynucleotide whenever the nuclease recognizing the site is applied. The size of "r" in a particular embodiment depends on the reach of the nuclease (as the term is defined in U.S. Pat. No. 5,599,675) and the number of nucleotides sought to be cleaved from the target polynucleotide. Preferably, r is between 0 and 20; more preferably, r is between 0 and 12. The region of "q" nucleotide pairs is a spacer segment between the nuclease recognition site and the tag region of the encoded probe. The region of "q" nucleotide may include further nuclease recognition sites, labelling or signal generating moieties, or the like. The single stranded oligonucleotide of "t" nucleotides is a "t-mer" oligonucleotide tag selected from a minimally cross-hybridizing set.

The 3' blocking group "z" may have a variety of forms and may include almost any chemical entity that precludes ligation and that does not interfere with other steps of the method, e.g. removal of the 3' blocked strand, ligation, or the like. Exemplary 3' blocking groups include, but are not limited to, hydrogen (i.e. 3' deoxy), phosphate, phosphorothioate, acetyl, and the like. Preferably, the 3' blocking group is a phosphate because of the convenience in adding the group during the synthesis of the 3' blocked strand and the convenience in removing the group with a phosphatase to render the strand capable of ligation with a ligase. An oligonucleotide having a 3' phosphate may be synthesized using the protocal described in chapter 12 of Eckstein, Editor, Oligonucleotides and Analogues: A Practical Approach (IRL Press, Oxford, 1991).

Further 3' blocking groups are available from the chemistries developed for reversable chain terminating nucleotides in base-by-base sequencing schemes, e.g. disclosed in the following references: Cheeseman, U.S. Pat. No. 5,302,509; Tsein et al, International application WO 91/06678; Canard et al, Gene, 148: 1–6 (1994); and Metzker et al, Nucleic Acids Research, 22: 4259–4267 (1994). Roughly, these chemistries permit the chemical or enzymatic removal of specific blocking groups (usually having an appendent label) to generative a free hydroxyl at the 3' end of a priming strand.

Preferably, when z is a 3' blocking group, it is a phosphate group and the double stranded portion of the adaptors contain a nuclease recognition site of a nuclease whose recognition site is separate from its cleavage site.

When double stranded oligonucleotide tags are employed that specifically hybridize with single stranded tag complements to form triplex structures, encoded tags of the invention preferably have the following form:

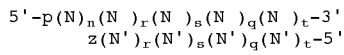

or

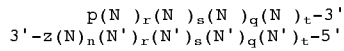

where N, N', p, q, r, s, z, and n are defined as above. Preferably, in his embodiment t is an integer in the range of 12 to 40.

Clearly, there are additional structures which contain elements of the basic designs set forth above that would be apparent to those with skill in the art. For example, encoded adaptors of the invention include embodiments with multiple tags, such as the following:

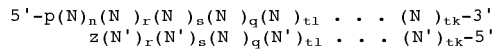

or

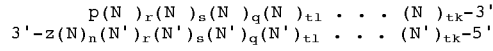

where the encoded adaptor includes k double stranded tags. Preferably, $t_1=t_2=\ldots t_k$ and k is either 1, 2, or 3.

Labeling Tag Complements

The tag complements of the invention can be labeled in a variety of ways for decoding oligonucleotide tag, including the direct or indirect attachment of radioactive moieties, fluorescent moieties, colorimetric moieties, chemiluminescent moieties, and the like. Many comprehensive reviews of methodologies for labeling DNA and constructing DNA adaptors provide guidance applicable to constructing adaptors of the present invention. Such reviews include Matthews et al, *Anal. Biochem.*, Vol 169, pgs. 1–25 (1988); Haugland, Handbook of Fluorescent Probes and Research Chemicals (Molecular Probes, Inc., Eugene, 1992); Keller and Manak, DNA Probes, 2nd Edition (Stockton Press, New York, 1993); and Eckstein, editor, Oligonucleotides and Analogues: A Practical Approach (IRL Press, Oxford, 1991); Wetmur, Critical Reviews in Biochemistry and Molecular Biology, 26: 227–259 (1991); and the like. Many more particular methodologies applicable to the invention are disclosed in the following sample of reference: Fung et al, U.S. Pat. No. 4,757,141; Hobbs, Jr., et al U.S. Pat. No. 5,151,507; Cruickshank, U.S. Pat. No. 5,091,519; (synthesis of functionalized oligonucleotides for attachment of reporter groups); Jablonski et al, Nucleic Acids Research, 14: 6115–6128 (1986)(enzyme-oligonucleotide conjugates); Ju et al, Nature Medicine, 2: 246–249 (1996); and Urdea et al, U.S. Pat. No. 5,124,246 (branched DNA). Attachment sites of labeling moieties are not critical, provided that such labels do not interfere with the ligation and/or cleavage steps.

Preferably, one or more fluorescent dyes are sued as labels for tag complements, e.g. as disclosed by Menchen et al, U.S. Pat. No. 5,188,934; Begot et al PCT application PCT/US90/05565. As used herein, the term "fluorescent signal generating moeity" means a signaling means which conveys information through the fluorescent absorption and/or emission properties of one or more molecules. Such fluorescent properties include fluorescence intensity, fluorescence life time, emission spectrum characteristics, energy transfer, and the like.

Ligating Adaptors and Preventing Self-Ligation

In accordance with the preferred embodiment of the invention, cleavage adaptors are ligated to the ends of target polynucleotides to prepare such ends for eventual ligation of encoded adaptors. Preferably, ligation is carried out enzymatically using a ligase in a standard protocol. Many ligases are known and are suitable for use in the invention, e.g. Lehman, Science, 186: 790–797 (1974); Engler et al, DNA Ligases, pages 3–30 in Boyer, editor, The Enzymes, Vol. 15B (Academic Press, New York, 1982); and the like. Preferred ligases include T4 DNA ligase, T7 DNA ligase, *E. coil* DNA ligase, Taq ligase, Pfu ligase, and Tth ligase. Protocols for their use are well known, e.g. Sambrook et al (cited above); Barany, PCR Methods an Applications, 1: 5–16 (1991); Marsh et al, Strategies, 5: 73–76 (1992); and the like. Generally, ligases require that a 5' phosphate group be present for ligation to the 3' hydroxyl of an abutting strand. This is conveniently provided for at least one strand of the target polynucleotide by selecting a nuclease which leaves a 5' phosphate, e.g. as Fok I.

Figure 2:
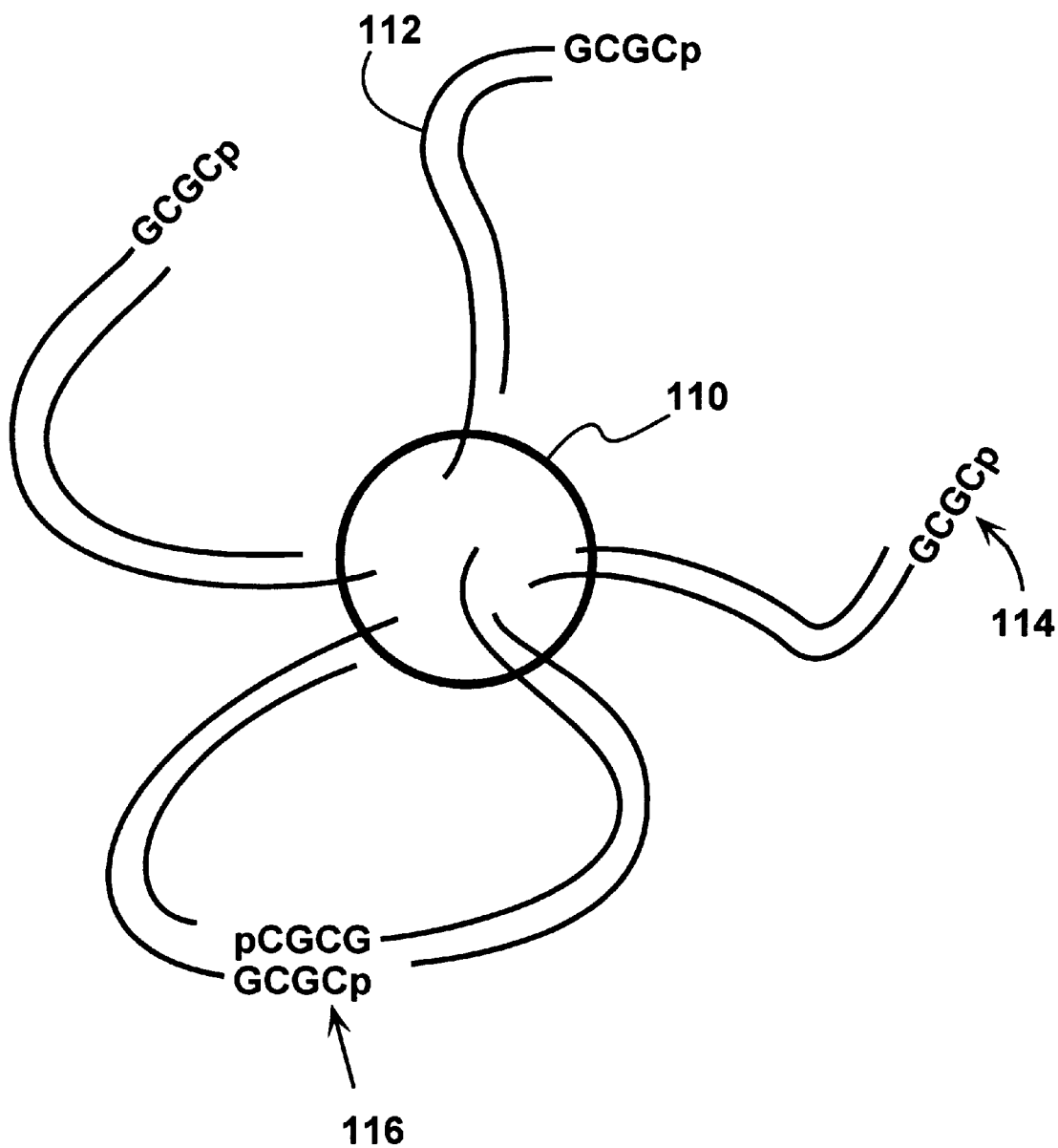
FIG. 2 illustrates the phenomena of self-ligation of identical polynucleotides that are anchored to a solid phase support.

A special problem may arise in dealing with either polynucleotide ends or adaptors that are capable of self-ligation, such as illustrated in FIG. 2, where the four-nucleotide protruding strands of the anchored polynucleotides are complementary to one another (114). This problem is especially sever in embodiments where the polynucleotides (112) to be analyzed are presented to the adaptors as uniform populations of identical polynucleotides attached to a solid phase support (100). In these situations, the free ends of the anchored polynucleotides can twist around to form perfectly matched duplexes (116) with one another. If the 5' strands of the ends are phosphorylated, the polynucleotides are readily ligated in the presence of a ligase. An analogous problem also exists for double stranded adaptors. Namely, whenever their 5' strands are phosphorylated, the 5' strand of one adaptor may be ligated to the free 3' hydroxyl of another adaptor whenever the nucleotide sequences of their protruding strands are complementary. When self-ligation occurs, the protruding strands of neither the adaptors nor the target polynucleotides are available for analysis or processing. This, in turn, leads to the loss or disappearance of signals generated in response to correct ligations of adaptors to target polynucleotides. Since the probability of a palindromic 4-mer occurring in a random sequence is the same as the probability of a repeated pair of nucleotides (6.25%), adaptor-based methods for de novo sequencing have a high expectation of failure after a few cycles because of self-ligation. When this occurs, further analysis of the polynucleotide becomes impossible.

Figure 3A:
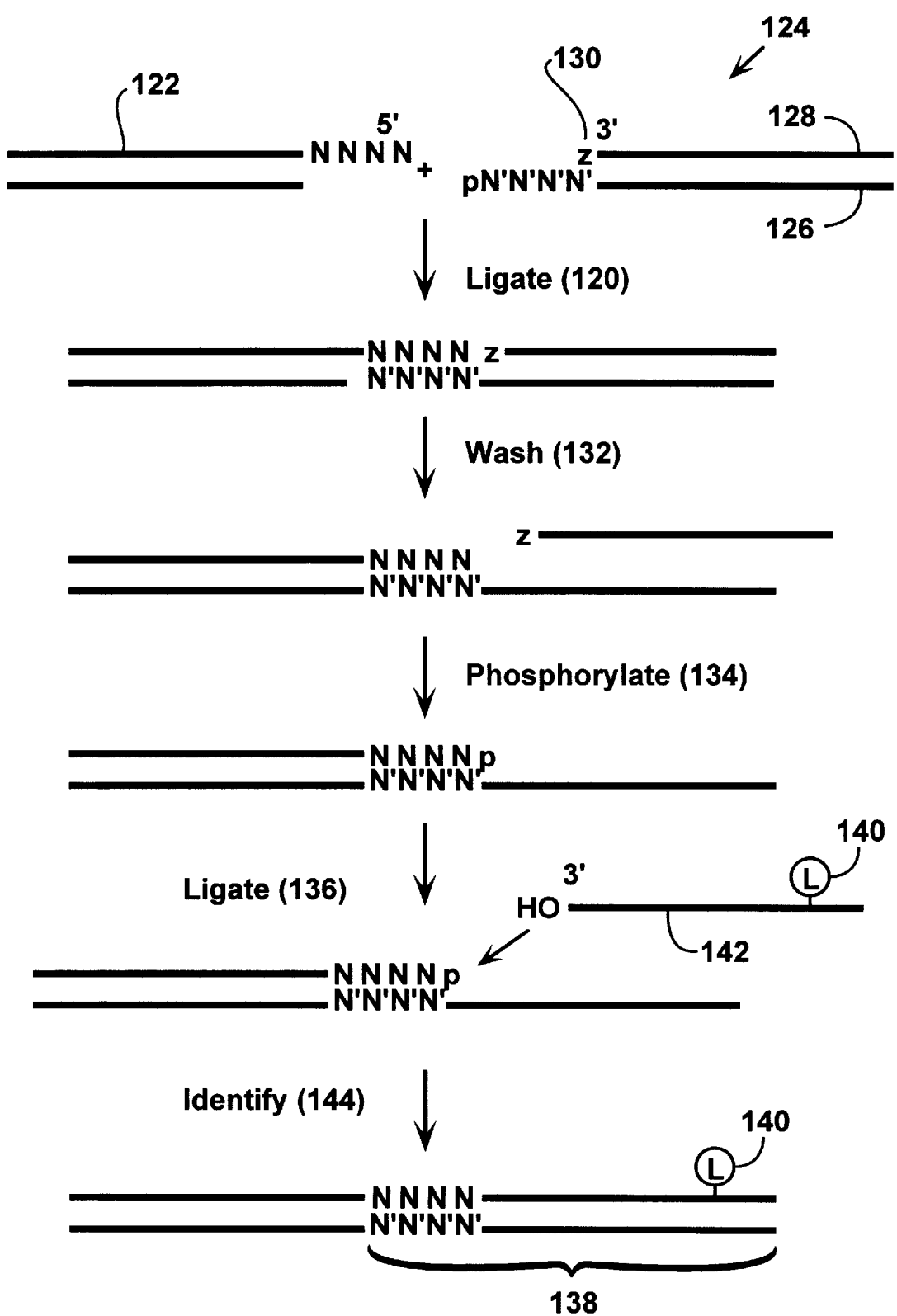
FIG. 3a illustrates steps in a preferred method of the invention in which a double stranded adaptor having a blocked 3' carbon is ligated to a target polynucleotide.
Figure 3B:
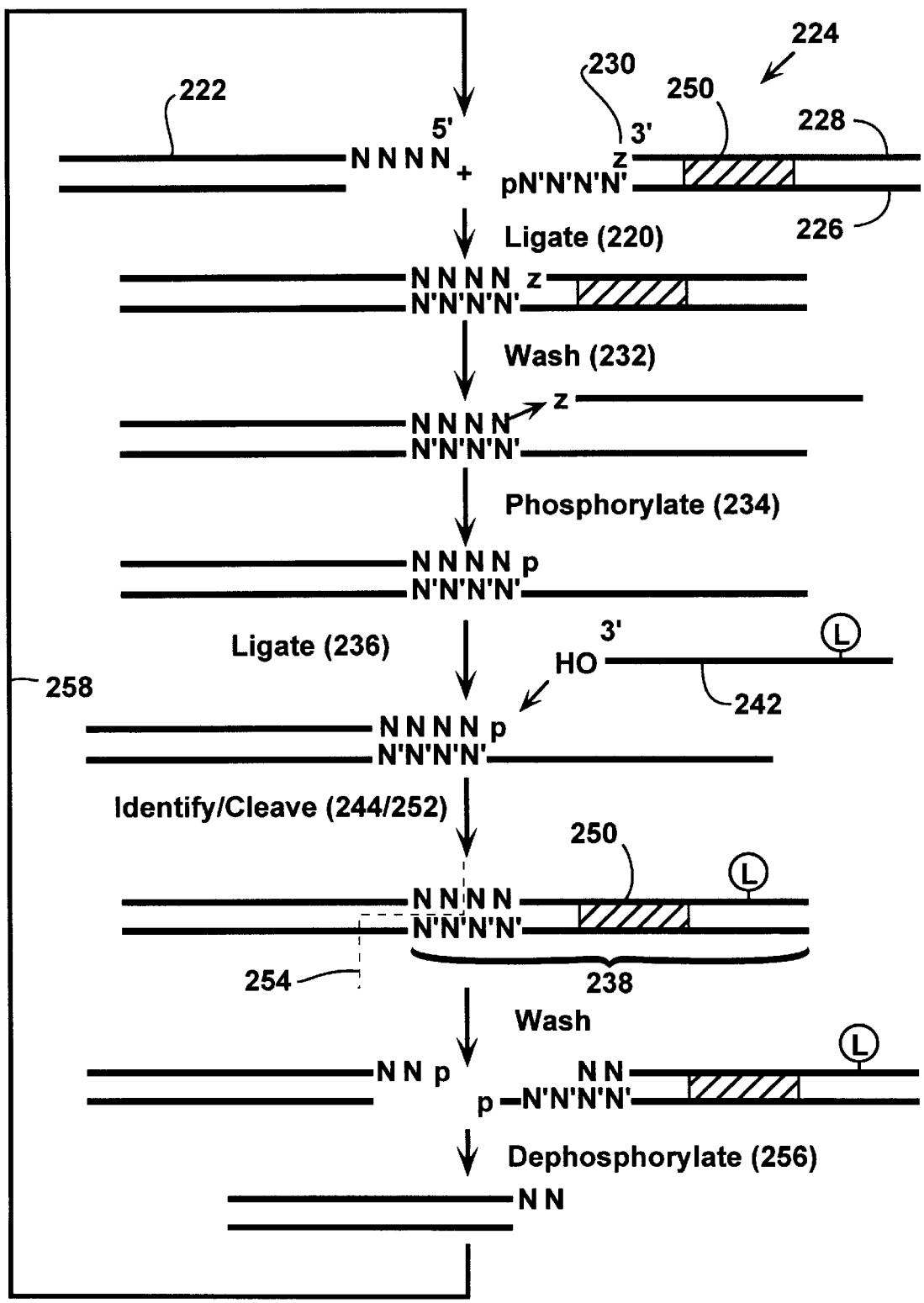
FIG. 3b illustrates the use of the preferred embodiment in a method of DNA sequencing by stepwise cycles of ligation and cleavage.

The above problems may be addressed by implementing the invention in the following steps, which are illustrated in FIG. 3a for a preferred embodiment: (a) ligating (120) an encoded adaptor to an end of the polynucleotide (122), the end of the polynucleotide having a dephosphorylated 5' hydroxyl and the end of the encoded adaptor (124) to be ligated having a first strand (126) and a second strand (128), the second strand of the encoded adaptor having a 3' blocking group (130); (b) removing the 3' blocking group of the second strand after ligation, e.g. by washing (132), or by enzymatically or chemically removing the group in situ, e.g. by treatment with a phosphatase if the blocking group is a phosphate; (c) phosphorylating (134) the 5' hydroxyl of the polynucleotide; (d) ligating (136) a second strand (142) having an unblocked 3' moiety to regenerate the encoded adaptor (138); and (e) identifying (144) one or more nucleotides at the end of the polynucleotide by the identity of the encoded adaptor ligated thereto, e.g. via a fluorescently labelled (140) tag complement. The encoded adaptors and target polynucleotides may be combined for ligation either singly or as mixtures. For example, a single kind of adaptor having a defined sequence may be combined with a single kind of polynucleotide having a common (and perhaps, unknown) nucleotide sequence; or a single kind of adaptor having a defined sequence may be combined with a mixture of polynucleotides, such as a plurality of uniform populations of identical polynucleotides attached to different solid phase supports in the same reaction vessel, e.g. described by Brenner et al, International application PCT/US96/09513; or a mixture of encoded adaptors, particularly mixtures having different nucleotide sequences in their protruding strands, may be combined with a single kind of polynucleotide; or a mixture of encoded adaptors may be combined with a mixture of polynucleotides. When the term "adaptor", or "encoded adaptor," is used in the singular it is meant to encompass mixtures of adaptors having different sequences of protruding strands as well as a single kind of adaptor having he same sequence of protruding strand, in a manner analogous to the usage of the term "probe."

Besides removing by melting, a 3' deoxy may be removed from a second strand by a polymerase "exchange" reaction disclosed in Kuijper et al, Gene, 112: 147–155 (1992); Aslanidis et al, Nucleic Acids Research, 18: 6069–6074 (1990); and like reference. Briefly, the 5'→3' exonuclease activity of T4 DNA polymerase, and like enzymes, may be used to exchange nucleotides in a priming strand with their triphosphate counterparts in solution, e.g. Kuijper et al (cited above). Thus, with such a reaction a 3' dideoxynucleotide can be exchanged with a 2'-deoxy-3'-hydroxynucleotide from a reaction mixture, which would render the second strand ligatable to the target polynucleotide after treatment with a polynucleotide kinase.

A preferred embodiment employing cycles of ligation and cleavage comprises the following steps: (a) ligating (220) an encoded adaptor to an end of the polynucleotide (222), the end of the polynucleotide having a dephosphorylated 5' hydroxyl, the end of the double stranded adaptor to be ligated (224) having a first strand (226) and a second strand (228), the second strand of the double stranded adaptor having a 3' blocking group (230), and the double stranded adaptor having a nuclease recognition site (250) of a nuclease whose recognition site is separate from its cleavage site; (b) removing the 3' blocking group after ligation, e.g. by washing off the second strand (232); (c) phosphorylating (234) the 5' hydroxyl of the polynucleotide; (d) ligating (236) a second strand (242) having an unblocked 3' moiety to regenerate the double stranded adaptor (238) and the nuclease recognition site (250); (e) identifying (244) one or more nucleotides at the end of the polynucleotide by the identity of the adaptor ligated thereto; (of) cleaving (252) the polynucleotide with a nuclease that recognizes the recognition site such that the polynucleotide is shortened by one or more nucleotides, the recognition site being positioned in the illustrated adaptor (224) so that the cleavage (254) removes two nucleotides from polynucleotide (222); (g) dephosphorylating (256) the 5' end of the polynucleotide; and (h) repeating (258) steps (a) through (g).

Typically, prior to ligation, ends of polynucleotides to be analyzed are prepared by digesting them with one or more restriction endonucleases that produce predetermined cleavages, usually having 3' or 5' protruding strands, i.e. "sticky" ends. Such digestions usually leave the 5' strands phosphorylated. Preferably, these 5' phosphorylated ends are dephosphorylated by treatment with a phosphatase, such as calf intestinal alkaline phosphatase, or like enzyme, using standard protocols, e.g. as described in Sambrook et al, Molecular Cloning, Second Edition (Cold Spring Harbor Laboratory, New York, 1989). By removal of the 5' phosphates the target polynucleotides are rendered incapable of being ligated in the presence of a ligase. The step of dephosphorylating preferably leaves a free 5' hydroxyl.

Preferred Nucleases

"Nuclease" as the term is used in accordance with the invention means any enzyme, combination of enzymes, or other chemical reagents, or combinations chemical reagents and enzymes that when applied to a ligated complex, discussed more fully below, cleaves the ligated complex to produce an augmented adaptor and a shortened target polynucleotide. A nuclease of the invention need not be a single protein, or consist solely of a combination of proteins. A key feature of the nuclease, or of the combination of reagents employed as a nuclease, is that is (their) cleavage site be separate from its (their) recognition site. The distance between the recognition site of a nuclease and its cleavage site will be referred to herein as its "reach." By convention, "reach" is defined by two integers which give the number of nucleotides between the recognition site and the hydrolyzed phosphodiester bonds of each strand. For example, the recognition and cleavage properties of Fok I is typically represented as "GGATG(9/13)" because it recognizes and cuts a double stranded DNA as follows (SEQ ID NO: 2):

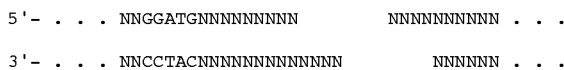

where the bolded nucleotides are Fok I's recognition site and the N's are arbitrary nucleotides and their complements.

It is important that the nuclease only cleave the target polynucleotide after it forms a complex with its recognition site; and preferably, the nuclease leaves a protruding strand on the target polynucleotide after cleavage.

Preferably, nucleases employed in the invention are natural protein endonucleases (i) whose recognition site is separate from its cleavage site and (ii) whose cleavage results in a protruding strand on the target polynucleotide. Most preferably, class IIs restriction endonucleases are employed as nucleases in the invention, e.g. as described in Szybalski et al, Gene, 100: 13–26 (1991); Roberts et al, Nucleic Acids Research, 21: 3125–3137 (1993); and Livak and Brenner, U.S. Pat. No. 5,093,245. Exemplary class IIs nucleases for use with the invention include Alw XI, Bsm AI, Bbv I, Bsm FI, Sts I, Hga I, Bsc AI, Bbv II, Bce fI, Bce 851, Bcc I, Bcg I, Bsa I, Bsg I, Bsp MI, Bst 71 I, Ear I, Eco 571, Esp 31, Fau I, Fol I, Gsu I, Hph I, Mbo II, Mme I, Rle AI, Sap I, Sfa NI, Taq II, Tth IIIII, Bco 51, Bpu AI, Fin I, Bsr DI, and isoschizomers thereof. Preferred nucleases include Bbv I, Fok I, Hga I, Ear I, and Sfa NI. Bbv I is the most preferred nuclease.

Preferably, prior to nuclease cleavage steps, usually at the start of a sequencing operation, the target polynucleotide is treated to block the recognition sites and/or cleavage sites of the nuclease being employed. This prevents undesired cleavage of the target polynucleotide because of the fortuitous occurrence of nuclease recognition sites at interior locations in the target polynucleotide. Blocking can be achieved in a variety of ways, including methylation and treatment by sequence-specific aptamers, DNA binding proteins, or oligonucleotides that form triplexes. Whenever natural protein endonucleases are employed, recognition sites can be conveniently blocked by methylating the target polynucleotide with the cognate methylase of the nuclease being used. That is, for most if not all type II bacterial restriction endonucleases, there exists a so-called "cognate" methylase that methylates its recognition site. May such emthylases are disclosed in Roberts et al (cited above) and Nelson et al, Nucleic Acids Research, 21: 3139–3154 (1993), and are commerically available from a variety of sources, particularly New England Biolabs (Beverly, Mass.). Alternatively, if a PCR step is employed in preparing target polynucleotides for sequencing, 5-methylcytosine triphosphates may be used during amplification so that the natural cytosine are replace by methylated cytosines in the amplicon. This later approach has the added advantage of eliminating the need to treat a target polynucleotide bound to a solid phase support with another enzyme.

Clearly, one of ordinary skill in the art could combine features of the embodiments set forth above to design still further embodiments in accordance with the invention, but not expressly set forth above.

A variety of kits are provided for carrying out different embodiments of the invention. Generally, kits of the invention include encoded adaptors, cleavage adaptors, and labeled tag complements. Kits further include the nuclease reagents, the ligation reagents, and instructions for practicing the particular embodiment of the invention. In embodiments employing natural protein endonucleases and ligases, ligase buffers and nuclease buffers may be included. In some cases, these buffers may be identical. Such kits may also include a methylase and its reaction buffer. Preferably, kits also include one or more solid phase supports, e.g. microparticles carrying tag complements for sorting and anchoring target polynucleotides.

Attaching Tags to Polynucleotides For Sorting onto Solid Phase Supports

An important aspect of the invention is the sorting and attachment of a populations of polynucleotides, e.g. from a cDNA library, to microparticles or to separate regions on a solid phase support such that each microparticle or region has substantially only one kind of polynucleotide attached. This objective is accomplished by insuring that substantially all different polynucleotides have different tags attached. This condition, in turn, is brought about by taking a sample of the full ensemble of tag-polynucleotide conjugates for analysis. (It is acceptable that identical polynucleotides have different tags, as it merely results in the same polynucleotide being operated on or analyzed twice in two different locations.) Such sampling can be carried out either overtly—for example, by taking a small volume from a larger mixture—after the tags have been attached to the polynucleotides, it can be carried out inherently as a secondary effect of the techniques used to process the polynucleotides and tags, or sampling can be carried out both overtly and as an inherent part of processing steps.

Preferably, in constructing a cDNA library where substantially all different cDNAs have different tags, a tag repertoire is employed whose complexity, or number of distinct tags, greatly exceeds the total number of mRNAs extracted from a cell or tissue sample. Preferably, the complexity of the tag repertoire is at least 10 times that of the polynucleotide population; and more preferably, the complexity of the tag repertoire is at least 100 times that of the polynucleotide population. Below, a protocol is disclosed for cDNA library construction using a primer mixture that contains a full repertoire of exemplary 9-word tags. Such a mixture of tag-containing primers has a complexity of $8^9$, or about $1.34 \times 10^8$. As indicated by Winslow et al, Nucleic Acids Research, 19: 3251–3253 (1991), mRNA for library construction can be extracted from as few as 10–100 mammalian cells. Since a single mammalian cell contains about $5 \times 10^5$ copies of mRNA molecules of about $3.4 \times 10^4$ different kinds, by standard techniques one can isolate the mRNA from about 100 cells, or (theoretically) about $5 \times 10^7$ mRNA molecules. Comparing this number to the complexity of the primer mixture shows that without any additional steps, and even assuming that mRNAs are converted into cDNAs with perfect efficiency (1% efficiency or less is more accurate), the cDNA library construction protocol results in a population containing nor more than 37% of the total number of different tags. That is, without any overt sampling step at all, the protocol inherently generates a sample that comprises 37%, or less, of the tag repertoire. The probability of obtaining a double under these conditions is about 5%, which is within the preferred range. With mRNA from 10 cells, the fraction of the tag repertoire sampled is reduced to only 3.7%, even assuming that all the processing steps take place at 100% efficiency. In fact, the efficiencies of the processing steps for constructing cDNA libraries are very low, a "rule of thumb" being that good library should contain about $10^8$ cDNA clones from mRNA extracted from $10^6$ mammalian cells.

Use of larger amounts of mRNA in the above protocol, or for larger amounts of polynucleotides in general, where the number of such molecules exceeds the complexity of the tag repertoire, a tag-polynucleotide conjugate mixture potentially contains every possible pairing of tags and types of mRNA or polynucleotide. In such cases, overt sampling may be implemented by removing a sample volume after a serial dilution of the starting mixture of tag-polynucleotide conjugates. The amount of dilution required depends on the amount of starting material and the efficiencies of the processing steps, which are readily estimated.

If mRNA were extracted from $10^6$ cells (which would correspond to about 0.5 μg of poly(A)$^+$RNA), and if primers were present in about 10–100 fold concentration excess—as is called for in a typical protocol, e.g. Sambrook et al, Molecular Cloning, Second Edition, page 8.61 [10 μL 1.8 kb mRNA at 1 mg/mL equals about $1.68 \times 10^{-11}$ moles and 10 μL 18-mer primer at 1 mg/mL equals about $1.68 \times 10^{-9}$ moles], then the total number of tag-polynucleotide conjugates in a cDNA library would simply be equal to or less than the starting number of mRNAs, or about $5 \times 10^{11}$ vectors containing tag-polynucleotide conjugates—again this assumes that each step in cDNA construction—first strand synthesis, second strand synthesis, ligation into a vector—occurs with perfect efficiency, which is a very conservative estimate. The actual number is significantly less.

If a sample of n tag-polynucleotide conjugates are randomly drawn from a reaction mixture—as could be effected by taking a sample volume, the probability of drawing conjugates having the same tag is described by the Poisson distribution, $P(r)=e^{-\lambda}(\lambda)^r/r$, where r is the number of conjugates having the same tag and $\lambda=np$, where p is the probability of a given tag being selected. If $n=10^6$ and $p=1/(1.34 \times 10^8)$, then $\lambda=0.00746$ and $P(2)=2.76 \times 10^{-5}$. Thus, a sample of one million molecules gives rise to an expected number of doubles well within the preferred range. Such a sample is readily obtained as follows: Assume that the $5 \times 10^{11}$ mRNAs are perfectly converted into $5 \times 10^{11}$ vectors with tag-cDNA conjugates as inserts and that the $5 \times 10^{11}$ vectors are in a reaction solution having a volume of 100 μl. Four 10-fold serial dilutions may be carried out by transferring 10 μl from the original solution into a vessel containing 90 μl of an appropriate buffer, such as TE. This process may be repeated for three additional dilutions to obtain a 100 μl solution containing $5 \times 10^5$ vector molecules per μl. A 2 μl aliquot from this solution yields $10^6$ vectors containing tag-cDNA conjugates as inserts. This sample is then amplified by straight forward transformation of a competent host cell followed by culturing.

Of course, as mentioned above, no step in the above process proceeds with perfect efficiency. In particular, when vectors are employed to amplify a sample of tag-polynucleotide conjugates, the step of transforming a host is very inefficient. Usually, no more than 1% of the vectors are taken up by the host and replicated. Thus, for such a method of amplification, even fewer dilutions would be required to obtain a sample of $10^6$ conjugates.

A repertoire of oligonucleotide tags can be conjugated to a population of polynucleotides in a number of ways, including direct enzymatic ligation, amplification, e.g. via PCR, using primers containing the tag sequences, and the like. The initial ligating step produces a very large population of tag-polynucleotide conjugates such that a single tag is generally attached to many different polynucleotides. However, as noted above, by taking a sufficiently small sample of the conjugates, the probability of obtaining "doubles," i.e. the same tag on two different polynucleotides, can be made negligible. Generally, the larger the sample the greater the probability of obtaining a double. Thus, a design trade-off exists between selecting a large sample of tag-polynucleotide conjugates—which, for example, ensures adequate coverage of a target polynucleotide in a shotgun sequencing operation or adequate representation of a rapidly changing mRNA pool, and selecting a small sample which ensures that a minimal number of doubles will be present. In most embodiments, the presence of doubles merely ads an additional source of noise or, in the case of sequencing, a minor complication in scanning and signal processing, as microparticles giving multiple fluorescent signals can simply be ignored.

As used herein, the term "substantially all" in reference to attaching tags to molecules, especially polynucleotides, is meant to reflect the statistical nature of the sampling procedure employed to obtain a population of tag-molecule conjugates essentially free of doubles. The meaning of substantially all in terms of actual percentages of tag-molecule conjugates depends on how the tags are being employed. Preferably, for nucleic acid sequencing, substantially all means that at least eighty percent of the polynucleotides have unique tags attached. More preferably, it means that at least ninety percent of the polynucleotides have unique tags attached. Still more preferably, it means that at least ninety-five percent of the polynucleotides have unique tags attached. And, most preferably, it means that at least ninety-nine percent of the polynucleotides have unique tags attached.

Preferably, when the population of polynucleotides consists of messenger RNA (mRNA), oligonucleotides tags may be attached by reverse transcribing the mRNA with a set of primers preferably containing complements of tag sequences. An exemplary set of such primers could have the following sequence:

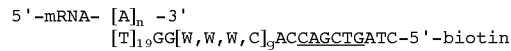

```
5'-mRNA- [A]_n -3'
         [T]_19GG[W,W,W,C]_9ACCAGCTGATC-5'-biotin
``` where "[W,W,W,C]$_9$" represents the sequence of an oligonucleotide tag of nine subunits of four nucleotides each and "[W,W,W,C]" represents the subunit sequences listed above, i.e. "W" represents T or A. The underlined sequences identify an optional restriction endonuclease site that can be used to release the polynucleotide from attachment to a solid phase support via the biotin, if one is employed. For the above primer, the complement attached to a microparticle could have the form:

```
5'-[G,W,W,W]_9TGG-linker-microparticle
```

After reverse transcription, the mRNA is removed, e.g. by RNase H digestion, and the second strand of the cDNA is synthesized using, for example, a primer of the following form (SEQ ID NO: 3):

```
5'-NRRGATCYNNN-3'
``` where N is any one of A, T, G, or C; R is a purine-containing nucleotide, and Y is a pyrimidine-containing nucleotide. This particular primer creates a Bst Y1 restriction site in the resulting double stranded DNA which, together with the Sal I site, facilitates cloning into a vector with, for example, Bam HI and Xho I sites. After Bst Y1 and Sal I digestion, the exemplary conjugate would have the form:

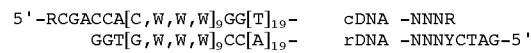

```
5'-RCGACCA[C,W,W,W]_9GG[T]_19-     cDNA  -NNNR
        GGT[G,W,W,W]_9CC[A]_19-    rDNA  -NNNYCTAG-5'
```

The polynucleotide-tag conjugates may then be manipulated using standard molecular biology techniques. For example, the above conjugate—which is actually a mixture—may be inserted into commercially available cloning vectors, e.g.

Stratagene Cloning System (La Jolla, Calif.); transfected into a host, such as a commerically available host bacteria; which is then cultured to increase the number of conjugates. The cloning vectors may then be isolated using standard techniques, e.g. Sambrook et al, Molecular Cloning, Second Edition (Cold Spring Harbor Laboratory, New York, 1989). Alternatively, appropriate adaptors and primers may be employed so that the conjugate population can be increased by PCR.

Preferably, when the ligase-based method of sequencing is employed, the Bst Y1 and Sal I digested fragments are cloned into a Bam HI-/Xho I-digested vector having the following single-copy restriction sites:

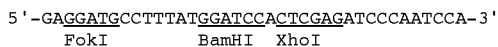

```
5'-GAGGATGCCTTTATGGATCCACTCGAGATCCCAATCCA-3'
    FokI        BamHI  XhoI
```

This adds the Fok I site which will allow initiation of the sequencing process discussed more fully below.

Tags can be conjugated to cDNAs of existing libraries by standard cloning methods. cDNAs are excised from their existing vector, isolated, and then ligated into a vector containing a repertoire of tags. Preferably, the tag-containing vector is linearized by cleaving with two restriction enzymes so that the excised cDNAs can be ligated in a predetermined orientation. The concentration of the linearized tag-containing vector is in substantial excess over that of the cDNA inserts so that ligation provides an inherent sampling of tags.

A generally method for exposing the single stranded tag after amplification involves digesting a target polynucleotide-containing conjugate with the 5'→3' exonuclease activity of T4 DNA polymerase, or a like enzyme. When used in the presence of a single deoxynucleoside triphosphate, such a polymerase will cleave nucleotides from 3' recessed ends present on the non-template strand of a double stranded fragment until a complement of the single deoxynucleoside triphosphate is reached on the template strand. When such a nucleotide is reached the 5'→3' digestion effectively ceases, as the polymerase's extension activity adds nucleotides at a higher rate than the excision activity removes nucleotides. Consequently, single stranded tags constructed with three nucleotides are readily prepared for loading onto solid phase supports.

The technique may also be used to preferentially methylate interior Fok I sites of a target polynucleotide while leaving a single Fok I site at the terminus of the polynucleotide unmethylated. First, the terminal Fok I site is rendered single stranded using a polymerase with deoxycytidine triphosphate. The double stranded portion of the fragment is then methylated, after which the single stranded terminus is filled in with a DNA polymerase in the presence of all four nucleoside triphosphates, thereby regenerating the Fok I site. Clearly, this procedure can be generalized to endonucleases other than Fok I.

After the oligonucleotide tags are prepared for specific hybridization, e.g. by rendering them single stranded as described above, the polynucleotides are mixed with microparticles containing the complementary sequences of the tags under conditions that favor the formation of perfectly matched duplexes between the tags and their complements. There is extensive guidance in the literature for creating these conditions. Exemplary references providing such guidance include Wetmur, Critical Reviews in Biochemistry and Molecular Biology, 26: 227–259 (1991); Sambrook et al, Molecular Cloning: A Laboratory Manual, 2nd Edition (Cold Spring Harbor Laboratory, New York, 1989); and the like. Preferably, the hybridization conditions are sufficiently stringent so that only perfectly matched sequences form stable duplexes. Under such conditions the polynucleotides specifically hybridized through their tags may be ligated to the complementary sequences attached to the microparticles. Finally, the microparticles are washed to remove polynucleotides with unligated and/or mismatched tags.

When CPG microparticles conventionally employed as synthesis supports are used, the density of tag complements on the microparticle surface is typically greater than that necessary for some sequencing operations. That is, in sequencing approaches that require successive treatment of the attached polynucleotides with a variety of enzymes, densely spaced polynucleotides may tend to inhibit access of the relatively bulky enzymes to the polynucleotides. In such cases, the polynucleotides are preferably mixed with the microparticles so that tag complements are present in significant excess, e.g. from 10:1 to 100:1, or greater, over the polynucleotides. This ensures that the density of polynucleotides on the microparticle surface will not be so high as to inhibit enzyme access. Preferably, the average inter-polynucleotide spacing on the microparticle surface is on the order of 30–100 nm. Guidance in selecting ratios for standard CPG supports and Ballotini beads (a types of solid glass support) is found in Maskos and Sourthern, Nucleic Acids Research, 20: 1679–1684 (1992). Preferably, for sequencing applications, standard CPG beads of diameter in the range of 20–50 $\mu$m are loaded with about $10^5$ polynucleotides, and glycidalmetharylate (GMA) beads available from Bands Laboratories (Carmel, Ind.) of diameter in the range of 5–10 $\mu$m are loaded with a few tens of thousand polynucleotide, e.g. $4 \times 10^4$ to $6 \times 10^4$.

In the preferred embodiment, tag complements for sorting are synthesized on microparticles combinatorially; thus, at the end of the synthesis, one obtains a complex mixture of microparticles from which a sample is taken for loading tagged polynucleotides. The size of the sample of microparticles will depend on several factors, including the size of the repertoire of tag complements, the nature of the apparatus for used for observing loaded microparticles—e.g. its capacity, the tolerance for multiple copies of microparticles with the same tag complement (i.e. "bead doubles"), and the like. The following table provide guidance regarding microparticle sample size, microparticle diameter, and the approximate physical dimensions of a packed array of microparticles of various diameters.

| Microparticle diameter | 5 $\mu$m | 10 $\mu$m | 20 $\mu$m | 40 $\mu$m |
|---|---|---|---|---|
| Max. no. polynucleotides loaded at 1 per $10^5$ sq. angstrom | | $3 \times 10^5$ | $1.26 \times 10^6$ | $5 \times 10^6$ |
| Approx. area of monolayer of $10^6$ microparticles | .45 × .45 cm | 1 × 1 cm | 2 × 2 cm | 4 × 4 cm |

The probability that the sample of microparticles contains a given tag complement or is present in multiple copies is described by the Poisson distribution, as indicated in the following table.

TABLE VI

| Number of microparticles in sample (as fraction of repertoire size), m | Fraction of repertoire of tag complements present in sample, $1-e^{-m}$ | Fraction of microparticles in sample with unique tag complement attached, $m(e^{-m})/2$ | Fraction of microparticles in sample carrying same tag complement as one other microparticle in sample ("bead doubles"), $m^2(e^{-m})/2$ |
|---|---|---|---|
| 1.000 | 0.63 | 0.37 | 0.18 |
| .693  | 0.50 | 0.35 | 0.12 |
| .405  | 0.33 | 0.27 | 0.05 |
| .285  | 0.25 | 0.21 | 0.03 |
| .223  | 0.20 | 0.18 | 0.02 |
| .105  | 0.10 | 0.09 | 0.005 |
| .010  | 0.01 | 0.01 | |

High Specificity Sorting and Panning

The kinetics of sorting depends on the rate of hybridization of oligonucleotide tags to their tag complements which, in turn, depends on the complexity of the tags in the hybridization reaction. Thus, a trade off exists between sorting rate and tag complexity, such that an increase in sorting rate may be achieved at the cost of reducing the complexity of the tags involved in the hybridization reaction. As explained below, the effects of this trade off may be ameliorated by "panning."

Specificity of the hybridizations may be increased by taking a sufficiently small sample so that both a high percentage of tags in the sample are unique and the nearest neighbors of substantially all the tags in a sample differ by at least two words. This latter condition may be met by taking a sample that contains a number of tag-polynucleotide conjugates that is about 0.1 percent or less of the size of the repertoire being employed. For example, if tags are constructed with eight words selected from Table II, a repertoire of $8^8$, or about $1.67 \times 10^7$, tags and tag complements are produced. In a library of tag-cDNA conjugates as described above, a 0.1 percent sample means that about 16,700 different tags are present. If this were loaded directly onto a repertoire-equivalent of microparticles, or in this example a sample of $1.67 \times 10^7$ microparticles, then only a sparse subset of the sampled microparticles would be loaded. The density of loaded microparticles can be increase—for example, for more efficient sequencing—by undertaking a "panning" step in which the sampled tag-cDNA conjugates are used to separate loaded microparticles from unloaded microparticles. Thus, in the example above, even through a "0.1 percent" sample contains only 16,700 cDNAs, the sampling and panning steps may be repeated until as many loaded microparticles as desired are accumulated. Alternatively, loaded microparticles may be separated from unloaded microparticles by a fluorescently activated cell sorting (FACS) instrument using conventional protocols, e.g. tag-cDNA conjugates may be fluorescently label in the technique described below by providing fluorescently labelled right primer. After loading and FACS sorting, the label may be cleaved prior to ligating encoded adaptors, e.g. by Dpn I or like enzyme that recognize methylated sites.

A panning step may be implemented by providing a sample of tag-cDNA conjugates each of which contains a capture moiety at an end opposite, or distal to, the oligonucleotide tag. Preferably, the capture moiety is of a type which can be released from the tag-cDNA conjugates, so that the tag-cDNA conjugates can be sequenced with a single-based sequencing method. Such moieties may comprise biotin, digoxigenin, or like ligands, a triplex binding region, or the like. Preferably, such a capture moiety comprises a biotin component. Biotin may be attached to tag-cDNA conjugates by a number of standard techniques. If appropriate adapters containing PCR primer binding sites are attached to tag-cDNA conjugates, biotin may be attached by using a biotinylated primer in an amplification after sampling. Alternatively, if the tag-cDNA conjugates are inserts of cloning vectors, biotin may be attached after excising the tag-cDNA conjugates by digestion with an appropriate restriction enzyme followed by isolation and filling in a protruding strand distal to the tags with a DNA polymerase in the presence of biotinylated uridine triphosphate.

After a tag-cDNA conjugate is captured, it may be released from the biotin moiety in a number of way, such as by a chemical linkage that is cleaved by reduction, e.g. Herman et al, Anal. Biochem., 156: 48–55 (1986), or that is cleaved photochemically, e.g. Olijnik et al, Nucleic Acids Research, 24: 361–366 (1996), or that is cleaved enzymatically by introducing a restriction site in the PCR primer. The latter embodiment can be exemplified by considering the library of tag-polynucleotide conjugates described above:

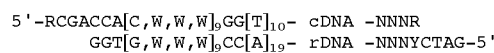

The following adapters may be ligated to the ends of these fragments to permit amplification by PCR:

Right Adapter

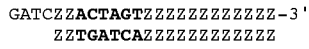

Left Adapter

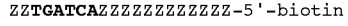

Left Primer where "ACTAGT" is a Spe I recognition site (which leaves a staggered cleavage ready for single base sequencing), and the X's and Z's are nucleotides selected so that the annealing and dissociation temperatures of the respective primers are approximately the same. After ligation of the adapters and amplification by PCR using the biotinylated primer, the tags of the conjugates are rendered single stranded by the exonuclease activity of T4 DNA polymerase and conjugates are combined with a sample of microparticles, e.g. a repertoire equivalent, with tag complements attached. After annealing under stringent conditions (to minimize mis-attachment of tags), the conjugates are preferably ligated to their tag complements and the loaded microparticles are separated from the unloaded microparticles by capture with avidinated magnetic beads, or like capture technique.

Returning to the example, this process results in the accumulation of about 10,500 (=16,700×0.63) loaded microparticles with different tags, which may be released from the magnetic beads by cleavage with Spe I. By repeating this process 40–50 times with new samples of microparticles and tag-cDNA conjugates, 4–5×10$^5$ cDNAs can be accumulated by pooling the released microparticles. The pooled microparticles may then be simultaneously sequenced by a single-based sequencing technique.

Left Primer

5'- AGTGGCTGGGCATCGGACCG

5'- AGTGGCTGGGCATCGGACCG- [$^4$(A,G,T)$_9$]-GGGGCCCAGTCAGCGTCGAT
    TCACCGACCCGTA<u>GCCTGGC</u>- [$^4$(A,G,T)$_9$]-<u>CCCCGGG</u>TCAGT<u>CGCAGCTA</u>

CCCCGGGTCAGTCGCAGCTA-5'

Right Primer

Determining how many times to repeat the sampling and panning steps—or more generally, determining how many cDNAs to analyze, depends on one's objective. If the objective is to monitor the changes in abundance of relatively common sequences, e.g. making up 5% or more of a population, then relatively small samples, i.e., a small fraction of the total population size, may allow statistically significant estimates of relative abundances. On the other hand, if one seeks to monitor the abundances of rare sequences, e.g. making up 0.1% or less of a population, then large samples are required. Generally, there is a direct relationship between sample size and the reliability of the estimates of relative abundances based on the sample. There is extensive guidance in the literature on determining appropriate sample sizes for making reliable statistical estimates, e.g. Koller et al, Nucleic Acids Research, 23:185–191 (1994); Good, Biometrika, 40: 16–264 (1953); Bunge et al. J. Am. Stat. Assoc., 88: 364–373 (1993); and the like. Preferably, for monitoring changes in gene expression based on the analysis of a series of cDNA libraries containing 10$^5$ to 10$^8$ independent clones of 3.0–3.5×10$^4$ different sequences, a sample of at least 10$^4$ sequences are accumulated for analysis of each library. More preferably, a sample of at least 10$^5$ sequences are accumulated for the analysis of each library; and most preferably, a sample of at least 5×10$^5$ sequences are accumulated for the analysis of each library. Alternatively, the number of sequences samples is preferably sufficient to estimate the relative abundance of a sequence present at a frequency within the range of 0.1% to 5% with a 95% confidence limit no larger than 0.1% of the population size.

Construction of a Tag Library

An exemplary tag library is constructed as follows to form the chemically synthesized 9-word tags of nucleotides, A, G, and T defined by the formula:

3'-TGGC-[$^4$(A,G,T)$_9$]-CCCC$_p$ where "[$^4$(A,G,T)$_9$]" indicates a tag mixture where each tag consists of nine 4-mer words of A, G, and T; and "p" indicate a 5' phosphate. This mixture is ligated to the following right and left primer binding regions (SEQ ID NO:4 & 5):

```
5'- AGTGGCTGGGCATCGGACCG      5'- GGGGCCCAGTCAGCGTCGAT
    TCACCGACCCGTAGCCp             GGGTCAGTCGCAGCTA

LEFT                            RIGHT
```

The right and left primer binding regions are ligated to the above tag mixture, after which the single stranded portion of the ligated structure is filled with DNA polymerase then mixed with the right and left primers indicated below and amplified to give a tag library.

The underlined portion of the left primer binding region indicates a Rsr II recognition site. The left-most underlined region of the right primer binding region indicates recognition sites for Bsp 120I, Apa I, and Eco O 109I, and a cleavage site for Hga I. The right-most underlined region of the right primer binding region indicates the recognition site for Hga I. Optionally, the right or left primers may be synthesized with a biotin attached (using conventional reagents, e.g. available from Clontech Laboratories, Palo Alto, Calif.) to facilitate purification after amplification and/or cleavage.

Construction of a Plasmid Library of Tag-
Polynucleotide Conjugates for cDNA "Signature"
Sequencing Using Encoded Adaptors cDNA is provided from anmRNA sample by conventional protocols using pGGCCCT$_{15}$(A or G or C) as a primer for first strand synthesis anchored at the boundary of the poly A region of the mRNAs and Ng(A or T)GATC as the primer for second strand synthesis. That is, both are degenerate primers such that the second strand primer is present in two forms and the first strand primer is present in three forms. The GATC sequence in the second strand primer corresponds to the recognition site of Mbo I; other four base recognition sites could be used as well, such as those for Bam HI, Sph I, Eco RI, or the like. The presence of the A and T adjacent to the restriction site of the second strand primer ensures that a stripping and exchange reaction can be used in the next step to generate a five-base 5' overhang of "GGCCC". The first strand primer is annealed to the mRNA sample and extended with reverse transcriptase, after which the RNA strand is degraded by the RNase H activity of the reverse transcriptase leaving a single stranded cDNA. The second strand primer is annealed and extended with a DNA polymerase using conventional protocols. After second strand synthesis, the resulting cDNAs are methylated with CpG methylase (New England Biolabs, Beverly, Mass.) using manufacturer's protocols. The 3' strands of the cDNAs are then cut back with the above-mentioned stripping and exchange reaction using T4 DNA polymerase in the present of dATP and dTTP, after which the cDNAs are ligated to the tag library described above previously cleaved with Hga I to give the following construct:

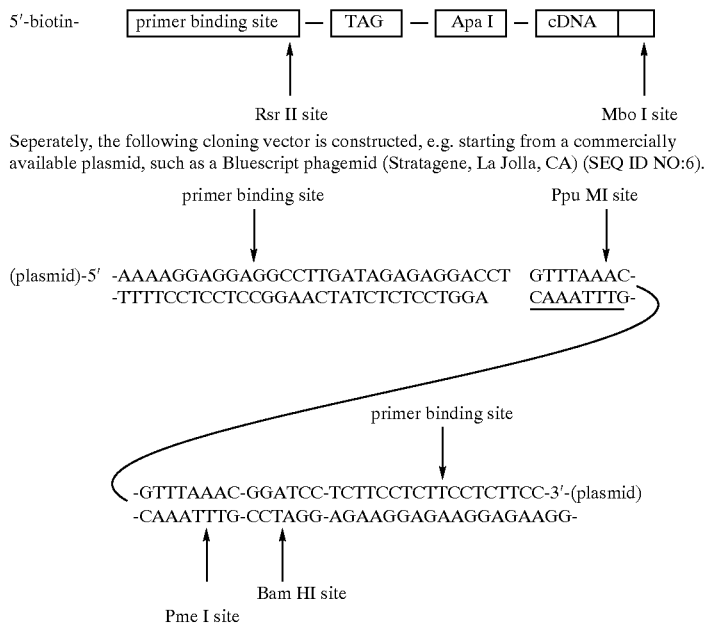

Seperately, the following cloning vector is constructed, e.g. starting from a commercially available plasmid, such as a Bluescript phagemid (Stratagene, La Jolla, CA) (SEQ ID NO:6).

The plasmid is cleaved with Ppu MI and Pme I (to give a Rsr II-compatible end and a flush end so that the insert is oriented) and then methylated with DAM methylase. The tag-containing construct is cleaved with Rsr II and then ligated to the open plasmid, after which the conjugate is cleaved with Mbo I and Bam HI to permit ligated and closing of the plasmid. The plasmids are then amplified and isolated for use in accordance with the invention.

EXAMPLE 1

Sequencing a Target Polynucleotide Amplified from pGEM7Z: Identification of Nucleotides by Cycles of Ligation and Cleavage In this example, a segment of plasmid pGEM7Z (Promega, Madison, Wis.) is amplified and attached to glass beads via a double stranded DNA linker, one strand of which is synthesized directly onto (and therefore covalently linked to) the beads. After the ends of the target polynucleotide are prepared for ligation to the encoded adapters, in each cycle of ligation and cleavage, a mixture of encoded adaptors (1024 different adaptors in all) is applied to the target polynucleotides so that only those adaptors whose protruding strands form perfectly matched duplexes with the target polynucleotides are ligated. Each of 16 fluoresently labelled tag complements are then applied to the polynucleotide-adaptor conjugates under conditions that permit hybridization of only the correct tag complements. The presence or absence of fluorescent signal after washing indicates the presence or absence of a particular nucleotide at a particular location. The sequencing protocol of this example is applicable to multiple target polynucleotides sorted onto one or more solid phase supports as described in Brenner, International patent applications PCT/US/95/12791 and PCT/US96/09513.

A 47-mer oligonucleotide is synthesized directly on Ballotini beads (0.040–0.075 mm, Jencons Scientific, Bridgeville, Pa.) using a standard automated DNA synthesizer protocol. The complementary strand to the 47-mer is synthesized separately and purified by HPLC. When hybridized the resulting duplex has a Bst XI restriction site at the end distal from the bead. The complementary strand is hybridized to the attached 47-mer in the following mixture; 25 µL, complementary strand at 200 pmol/µL; 20 mg Ballotini beads with the 47-mer; 6 µL New England Biolabs #3restriction buffer (form a 10× stock solution); and 25 µL distilled water. The mixture is heated to 93° C. and then slowly cooled to 55° C., after which 40 units of Bst XI (at 10 units/µL) is added to bring the reaction volume to 60 µL. The mixture is incubated at 55° C. for 2 hours after which the beads are washed three times in TE (pH 8.0).

The segment of pGEM7Z to be attached to the beads is prepared as follows: Two PCR primers were prepared using standard protocols (SEQ ID NO: 7 and SEQ ID NO: 8):

Primer 1: 5'-CTAAACCATTGGTATGGGCCAGTGAATTGTAATA

Primer 2: 5'-CGCGCAGCCCGCATCGTTTATGCTACAGACTGTC-

AGTGCAGCTCTCCGATCCAAA

The PCR reaction mixture consists of the following: 1 µl pGEM7Z at 1 ng/µL; 10 µl primer 1 at 10 pmol/µl; 10 µl primer 2 at 10 pmol/µl; 10 µl deoxyribonucleotide triphosphates at 2.5 mM; 10 µl 10× PCR buffer (Perkin-Elmer); 0.5 µl Taq DNA polymerase at 5 units/µl; and 58 µl distilled water to give a final volume of 100 µl. The reaction mixture was subjected to 25 cycles of 93° C. for 30 sec; 60° C. for 15 sec; and 72° C. for 60 sec, to give a 172 basepair product, which is successively digested with Bbv I (100 µl PCR reaction mixture, 12 µl 10× #1 New England Biolabs buffer, 8 µl Bbv I at 1 unit/µl incubate at 37° C. for 6 hours) and with Bst XI (to the Bbv I reaction mixture is added: 5 µl 1 M NaCl, 67 µl distilled water, and 8 µl Bst XI at 10 units/µl, and the resulting mixture is incubated at 55° C. for 2 hours).

After passing the above reaction mixture through a Centricon 30 (Amicon, Inc.) spin column following manufacturer's protocol, the Bbv I/Bst XI-restricted fragment is ligated to the double stranded linker attached to the Ballotini beads in the following mixture: 17 µl Bbv I/Bst XI-restricted fragment (10 µg), 10 µl beads (20 mg), 6 ml 10× ligated buffer (new England Biolabs, referred to below a NEB), 5 µl T4 DNA ligase at 2000 units/μl, and 22 μl distilled water, which mixture is incubated at 25° C. for 4 hours, after which the beads are washed 3 times with TE (pH 8.0), leaving the following target polynucleotide (SEQ ID NO:9) for sequencing having a 5' phosphate:

```
            . . . AGCTACCCGATC
[BEAD]-- . . . TCGATGGGCTAGATTTp-5'
```

The 5' phosphate is removed by treating the bead mixture with an alkaline phosphatase, e.g. from calf intestine, available from New England Biolabs (Beverly, Mass.), using manufacturer's protocol.

The top strands of the following 16 sets of 64 encoded adaptors (SEQ ID NO: 10 through SEQ ID NO: 25) are each separately synthesized on an automated DNA synthesizer (model 392 Applied Biosystems, Foster City) using standard methods. The bottom strand, which is the same for all adaptors, is synthesized separately then hybridized to the respective top strands:

| SEQIDNO. | EncodedAdaptor |
|---|---|
| 10 | 5'-pANNNTACAGCTGCATCCCttggcgctgagg<br>pATGCACGCGTAGGG-5' |
| 11 | 5'-pNANNTACAGCTGCATCCCtgggcctgtaag<br>pATGCACGCGTAGGG-5' |
| 12 | 5'-pCNNNTACAGCTGCATCCCttgacgggtctc<br>pATGCACGCGTAGGG-5' |
| 13 | 5'-pNCNNTACAGCTGCATCCCtgccgcacagt<br>pATGCACGCGTAGGG-5' |
| 14 | 5'-pGNNNTACAGCTGCATCCCttcgcctcggac<br>pATGCACGCGTAGGG-5' |
| 15 | 5'-pNGNNTACAGCTGCATCCCtgatccgctagc<br>pATGCACGCGTAGGG-5' |
| 16 | 5'-pTNNNTACAGCTGCATCCCttccgaacccgc<br>pATGCACGCGTAGGG-5' |
| 17 | 5'-pNTNNTACAGCTGCATCCCtgaggggggatag<br>pATGCACGCGTAGGG-5' |
| 18 | 5'-pNNANTACAGCTGCATCCCttcccgctacac<br>pATGCACGCGTAGGG-5' |
| 19 | 5'-pNNNATACAGCTGCATCCCtgactcccgag<br>pATGCACGCGTAGGG-5' |
| 20 | 5'-pNNCNTACAGCTGCATCCCtgtgttgcgcgg<br>pATGCACGCGTAGGG-5' |
| 21 | 5'-pNNNCTACAGCTGCATCCCtctacagcagcg<br>pATGCACGCGTAGGG-5' |
| 22 | 5'-pNNGNTACAGCTGCATCCCtgtcgcgtcgtt<br>pATGCACGCGTAGGG-5' |
| 23 | 5'-pNNNGTACAGCTGCATCCCtcggagcaacct<br>pATGCACGCGTAGGG-5' |
| 24 | 5'-pNNTNTACAGCTGCATCCCtggtgaccgtag<br>pATGCACGCGTAGGG-5' |
| 25 | 5'-pNNNTTACAGCTGCATCCCtcccctgtcgga<br>pATGCACGCGTAGGG-5' | where N and p are as defined above, the nucelotides indicated in lower case letters are the 12-mer oligonucleotide tags. Each tag differs from every other by 6 nucleotides. Equal molar quantities of each adaptor are combined in NEB #2 restriction buffer (New England Biolabs, Beverly, Mass.) to form a mixture at a concentration of 1000 pmol/μL.

Each of the 16 tag complements are separately synthesized as amino-derivatized oligonucleotides and are each labelled with a fluorescein molecule (using an NHS-ester of fluorescein, available from Molecular Probes, Eugene, Oreg.) which is attached to the 5' end of the tag complement through a polyethylene glycol linker (Clonetech Laboratories, Palo Alto, Calif.). The sequences of the tag complements are simply the 12-mer complements of the tags listed above.

Ligation of the adaptors to the target polynucleotide is carried out in a mixture consisting of 5 μl beads (20 mg), 3 μL NEB 10× ligase buffer, 5 μL adaptor mix (25 nM), 2.5 μL NEB T4 DNA ligase (2000 units/μL), and 14.5 μL distilled water. The mixture is incubated at 16° C. for 30 minutes, after which the beads are washed 3 times in TE (pH 8.0).

After centrifugation and removal of TE, the 3' phosphates of the ligated adaptors are removed by treating the polynucleotide-bead mixture with calf intestinal alkaline phosphatase (CIP) (New England Biolabs, Beverly, Mass.), using the manufacturer's protocol. After removal of the 3' phosphates, the CIP may be inactivated by proteolytic digestion, e.g. using Pronase™ (available from Boeringer Mannhiem, Indianapolis, Ind.), or an equivalent protease, with the manufacturer's protocol. The polynucleotide-bead mixture is then washed, treated with a mixture of T4 polynucleotide kinase and T4 DNA ligase (New England Biolabs, Beverly, Mass.) to add a 5' phosphate at the gap between the target polynucleotide and the adaptor, and to complete the ligation of the adaptors to the target polynucleotide. The bead-polynucleotide mixture is then washed in TE.

Separately, each of the labelled tag complements is applied to the polynucleotide-bead mixture under conditions which permit the formation of perfectly matched duplexes only between the oligonucleotide tags and their respective complements, after which the mixture is washed under stringent conditions, and the presence or absence of a fluorescent signal is measured. Tag complements are applied in a solution consisting of 25 nM tag complement 50 mM NaCl, 3 mM Mg, 10 mM Tris-HCl (pH 8.5), at 20° C., incubated for 10 minutes, then washed in the same solution (without tag complement) for 10 minutes at 55° C.

Figure 4:
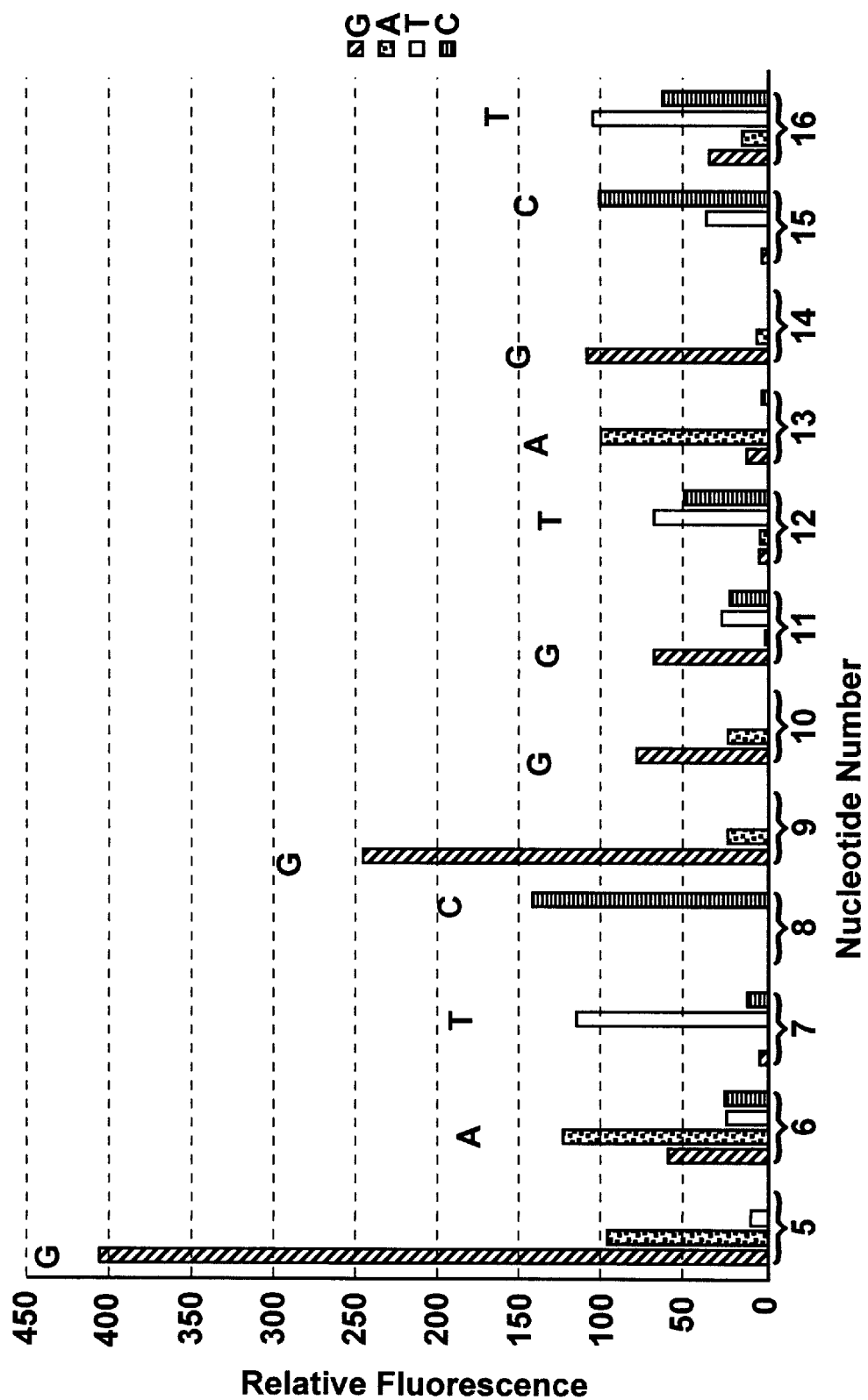
FIG. 4 illustrates data from the determination of the terminal nucleotides of a test polynucleotides using the method of the present invention.

After the four nucleotides are identified as described above, the encoded adaptors are cleaved from the polynucleotides with Bbv I using the manufacturer's protocol. After an initial ligation and identification, the cycle of ligation, identification, and cleavage is repeated three times to give the sequence of the 16 terminal nucleotides of the target polynucleotide. FIG. 4 illustrates the relative fluorescence from each of the four tag complements applied to identify nucleotides at positions 5 through 16 (from the most distal from the bead to the most proximal to the bead).

EXAMPLE 2

Construction and Sorting of cDNA Library for Signature Sequencing with Encoded Adaptors In this example, a cDNA library is constructed in which an oligonucleotide tag consisting of 8 four-nucleotide "words" is attached to each cDNA. As described above, the repertoire of oligonucleotide tags of this size is sufficiently large (about $10^8$) so that if the cDNAs are synthesized from a population of about $10^6$ mRNAs, then there is a high probability that each cDNA will have a unique tag for sorting. After mRNA extraction, first strand synthesis is carried out in the presence of 5-Me-dCTP (to block certain cDNA restriction sites) and a biotinylated primer mixture containing the oligonucleotide tags. After conventional second strand synthesis, the tag-cDNA conjugates are cleaved with Dpn II (which is unaffected by the 5-Me-deoxycytosines), the biotinylated portions are separated from the reaction mixture using streptavidin-coated magnetic beads, and the tag-cDNA conjugates are recovered by cleaving them from the magnetic beads via a Bsm BI site carried by the biotinylated primer. The Bsm BI-Dpn II fragment containing the tag-cDNA conjugate is then inserted into a plasmid and amplified. After isolation of the plasmids, tag-cDNA conjugates are amplified out of the plasmids by PCR in the presence of 5-Me-dCTP, using biotinylated and fluorescently labelled primers containing pre-defined restriction endonuclease sites. After affinity purification with streptavidin coated magnetic beads, the tag-cDNA conjugates are cleaved from the beads, treated with T4 DNA polymerase in the presence of dGTP to render the tags single stranded, and then combined with a repertoire of GMA beads having tag complements attached. After stringent hybridization and ligation, the GMA beads are sorted via FACS to produce an enriched population of GMA beads loaded with cDNAs. The enriched population of loaded GMA beads are immobilized in a planar array in a flow chamber where base-by-base sequence takes place using encoded adaptors.

Approximately 5 µg of poly(A+) mRNA is extracted from DBY746 yeast cells using conventional protocols. First and second strand cDNA synthesis is carried out by combining 100–150 pmoles of the following primer (SEQ ID NO:26):

with the poly(A+) mRNA using a Stratagene (LaJolla, Calif.) cDNA Synthesis Kit in accordance with the manufacturer's protocol. This results in cDNAs whose first stand deoxycytosines are methylated at the 5-carbon position. In the above formula, "V" is G, C, or A, "[W,W,W,G]" is a four-nucleotide word selected from Table II as described above, the single underlined portion is a Bsm BI recognition site, and the double underlined portion is a Pac I recognition site. After size fractionation (GIBCO-BRL cDNA Size Fractionation Kit) using conventional protocols, the cDNAs are digested with Dpn II (New England Bioscience, Beverly, Mass.) using manufactuer's protocol and affinity purified with streptavidin-coated magnetic beads (M-280 beads, Dynal A. S., Oslo, Norway). The DNA captured by the beads is digested with Bsm BI to release the tag-cDNA conjugates for cloning into a modified pBCSK− vector (Stratagene, La Jolla, Calif.) using standard protocols. The pBCSK− vector is modified by adding a Bbs I site by inserting the following fragment (SEQ ID NO:27) into the Kpn I/Eco RV digested vector.

Bsm BI/Dpn II digested tag-cDNA conjugate is inserted in the pBCSK− which is previously digested with Bbs I and Bam HI. After ligation, the vector is transfected into the manufacturer's recommended host for amplification.

After isolating the above pBCSK− vector from a standard plasmid miniprep, the tag-cDNA conjugates are amplified by PCR in the presence of 5-Me-dCTP using 20-mer primers complementary to vector sequences flanking the tag-cDNA insert. The "upstream" primer, i.e. adjacent to the tag, is biotinylated and the "downstream" primer, i.e. adjacent to the cDNA, is labelled with fluorecein. After amplification, the PCR product is affinity purified then cleaved with Pac I to relates fluorescently labelled tag-cDNA conjugates. The tags of the conjugates are rendered single stranded by treating them with T4 DNA polymerase in the presence of dGTP. After the reaction is quenched, the tag-cDNA conjugate is purified by phenol-chloroform extraction and combined with 5.5 µm GMA beads carrying tag complements, each tag complement having a 5' phosphate. Hybridization is conducted under stringent conditions in the presence of a thermal stable ligase so that only tags forming perfectly matched duplexes with their complements are ligated. The GM beads are washed and the loaded bead are concentrated by FACS sorting, using the fluorescently labelled cDNAs to identify loaded GMA beads. The tag-cDNA conjugates attached to the GMA beads are digested with Dpn II to remove the fluorescent label and treated with alkaline phosphatase to prepare the cDNAs for sequencing.

The following cleavage adaptor (SEQ ID NO:28) is ligated to the Dpn II-digested and phosphatase treated cDNAs:

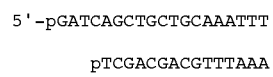

after which the 3' phosphate is removed by alkaline phosphatase, the 5' strand of the cDNA is treated with T4 DNA kinase, and the nick between the cleavage adaptor and cDNA is ligated. After cleavage by Bbv I, the encoded adaptors of Example 1 are ligated to the ends of the cDNAs as described above.

Figure 5:
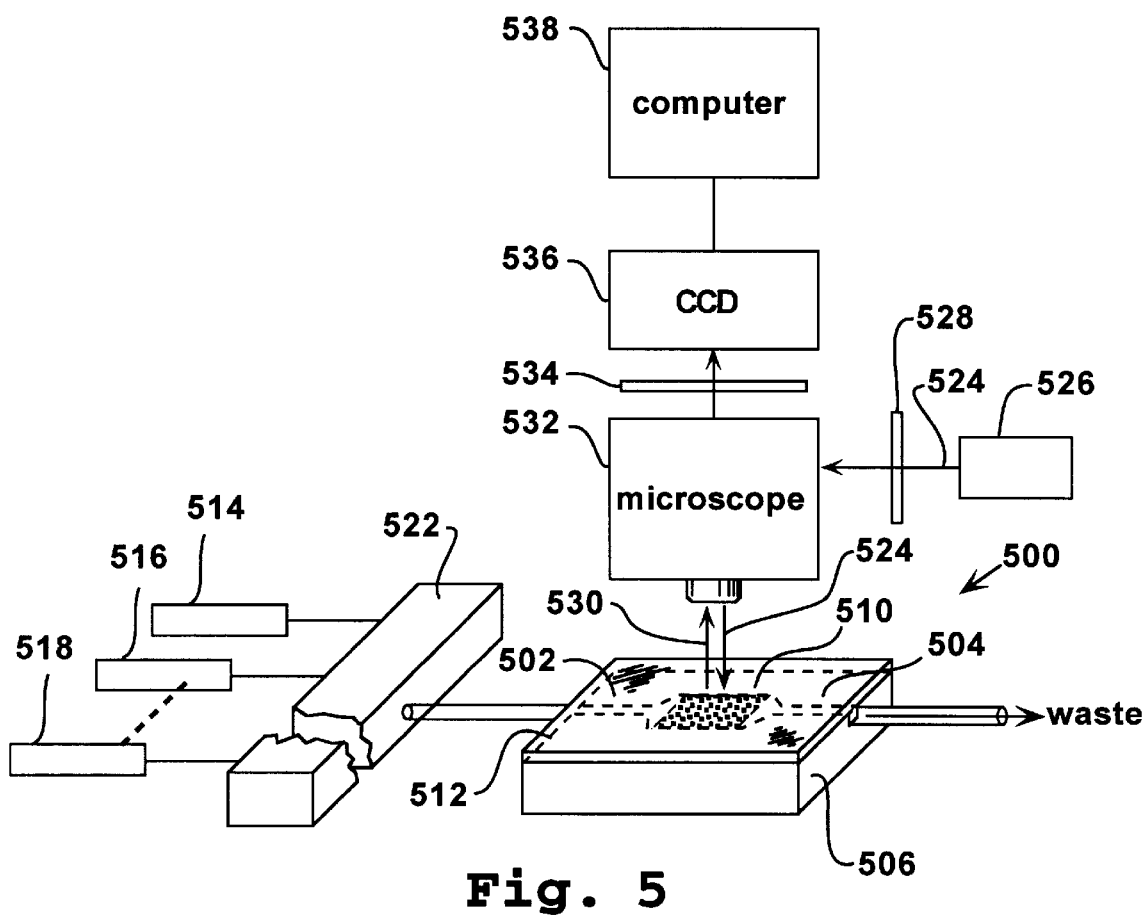
FIG. 5 is a schematic representation of a flow chamber and detection apparatus for observing a planar array of microparticles loaded with cDNA molecules for sequencing.

A flow chamber (500) diagrammatically represented in FIG. 5 is prepared by etching a cavity having a fluid inlet (502) and outlet (504) in a glass plate (506) using standard micromachining techniques, e.g. Ekstrom et al, International patent application PCT/SE91/00327; Brown, U.S. Pat. No. 4,911,782; Harrison et al, Anal. Chem. 64: 1926–1932 (1992); and the like. The dimension of flow chamber (500) are such that loaded microparticles (508), e.g. GMA beads, may be disposed in cavity (510) in a closely packed planar monolayer of 100–200 thousand beads. Cavity (510) is made into a closed chamber with inlet and outlet by anodic bonding of a glass cover slip (512) onto the etched glass plate (506), e.g. Pomerantz, U.S. Pat. No. 3,397,279. Reagents are metered into the flow chamber from syringe pumps (514 through 520) through valve block (522) controlled by a microprocessor as its commonly used on automated DNA and peptide synthesizers, e.g. Bridgham et al, U.S. Pat. No. 4,668,479; Hood et al. U.S. Pat. No. 4,252, 769; Barstow et al, U.S. Pat. No. 5,203,368; Hunkapiller, U.S. Pat. No. 4,703,913; or the like.

Three cycles of ligation, identification, and cleavage are carried out in flow chamber (500) to give the sequences of 12 nucleotides at the termini of each of approximately 100,000 cDNAs. Nucleotides of the cDNAs are identified by hybridizing tag complements to the encoded adaptors as described in Example 1. Specifically hybridized tag complements are detected by exciting their fluorescent labels with illumination beam (524) from light source (526), which may be a laser, mercury arc lamp, or the like. Illumination beam (524) passes through filter (528) and excites the fluorescent labels on tag complements specifically hybridized to encoded adaptors in flow chamber (500). Resulting fluorescence (530) is collected by confocal microscope (532), passes through filter (534), and directed to CCD camera (536), which creates an electronic image of the bead array for processing and analysis by workstation (538). Encoded adaptors and T4 DNA ligase (Promega, Madison, Wis.) at about 0.75 units per µL are passed through the flow chamber at a flow rate of about 1–2 μL per minute for about 20–30 minutes at 16° C., after which in succession a solution of Pronase™ (Boehringer Mannheim, Indianapolis, Ind.), a salt wash solution, and an ethanol wash solution are passed through the flow chamber, all with the same flow rate of 1–2 μL per minute and for durations of 15, 10, and 10 minutes, respectively. The salt wash solution is 150 mM NaCl and 10 mM Tris-HCl (pH 8.5), and the ethanol wash solution is 3:1 (v/v) solution of the salt wash solution and ethanol. The ligation, pronase, and wash steps are repeated once, after which 3' phosphates are removed from the adaptors and the cDNAs prepared for second strand ligation by passing a mixture of alkaline phosphatase (new England Bioscience, Beverly, Mass.) at 0.02 units per μL and T4 DNA kinase (New England Bioscience, Beverly, Mass.) at 7 units per μL through the flow chamber at 37° C. with a flow rate of 1–2 μL per minute for 15–20 minutes. Ligation of the second stand is carried out by flowing T4 DNA ligase (0.75 units per mL, Promega) through the flowchamber for 20–30 minutes at a rate of 1–2 μL per minute, followed by Pronase™ treatment and washing as described above. Tag complements at 25 nM concentration are passed through the flow chamber at a flow rate of 1–2 μL per minute for 10 minutes at 20° C., after which is fluorescent labels carried by the tag complements are illuminated and fluorescence is collected. The tag complements are melted from the encoded adaptors by passing NEB #2 restriction buffer with 3 mM $MgCl_2$ through the flow chamber at a flow rate of 1–2 μL per minute at 55° C. for 10 minutes. Encoded adaptors are cleaved from the cDNAs by passing Bbv I (New England Biosciences, Beverly, Mass.) at 1 unit/μL at a flow rate of 1–2 μL per minute for 20 minutes at 37° C., followed by Pronase™ treatment and washing, as described above.

APPENDIX I

Exemplary computer program for generating
minimally cross hybridizing sets
(single stranded tag/single stranded tag complement)

```
Program tagN
c
c       Program tagN generates minimally cross-hybridizing
c       sets of subunits given i) N--subunit length, and ii)
c       an initial subunit sequence. tagN assumes that only
c       3 of the four natural nucleotides are used in the tags.
c
c
        character*1 sub1(20)
        integer*2 mset(10000,20) nbase(20)
c
c
        write(*,*)'ENTER SUBUNIT LENGTH'
        read(*,100)nsub
100     format(i2)
c
c
        write(*,*)'ENTER SUBUNIT SEQUENCE'
        read(*,110) (sub1(k),k=1,nsub)
110     format(20al)
c
c
        ndiff=10
c
c
c             Let a=1 c=2 g=3 & t=4
c
c
        do 800 kk=1,nsub
        if(sub1(kk).eq.'a') then
            mset(1,k)=1
        endif
        if(sub1(kk).eq.'c') then
```

APPENDIX I-continued

Exemplary computer program for generating
minimally cross hybridizing sets
(single stranded tag/single stranded tag complement)

```
            mset(1,kk)=2
        endif
        if(sub1(kk).eq.'g') then
            mset(1,kk)=3
        endif
            if(sub1(kk).eq.'t') then
                mset(1,kk)=4
            endif
800     continue
c
c
c        Generate set of subunits differing from
c        sub1 by at least ndiff nucleotides.
c
c
        jj=1
c
c
        do 1000 k1=1,3
         do 1000 k2=1,3
          do 1000 k3=1,3
           do 1000 k4=1,3
            do 1000 k5=1,3
             do 1000 k6=1,3
              do 1000 k7=1,3
               do 1000 k8=1,3
                do 1000 k9=1,3
                 do 1000 k10=1,3
        do 1000 k11=1,3
         do 1000 k12=1,3
          do 1000 k13=1,3
           do 1000 k14=1,3
            do 1000 k15=1,3
             do 1000 k16=1,3
              do 1000 k17=1,3
               do 1000 k18=1,3
                do 1000 k19=1,3
                 do 1000 k20=1,3
c
c
            nbase(1)=k1
            nbase(2)=k2
            nbase(3)=k3
            nbase(4)=k4
            nbase(5)=k5
            nbase(6)=k6
            nbase(7)=k7
            nbase(8)=k8
            nbase(9)=k9
            nbase(10)=k10
            nbase(11)=k11
            nbase(12)=k12
            nbase(13)=k13
            nbase(14)=k14
            nbase(15)=k15
            nbase(16)=k16
            nbase(17)=k17
            nbase(18)=k18
            nbase(19)=k19
            nbase(20)=k20
c
c
        do 1250 nn=1,jj
c
        n=0
        do 1200 j=1,nsub
            if(mset(nn,j).eq.1 .and. nbase(j).ne.1 .or.
1               mset(nn,j).eq.2 .and. nbase(j).ne.2 .or.
2               mset(nn,j).eq.3 .and. nbase(j).ne.3 .or.
3               mset(nn,j).eq.4 .and. nbase(j).ne.4) then
            n=n+1
        endif
1200    continue
c
```

APPENDIX I-continued

Exemplary computer program for generating
minimally cross hybridizing sets
(single stranded tag/single stranded tag complement)

```
                if(n.lt.ndiff) then
                    goto 1000
                endif
1250        continue
c
c
                jj=jj+1
                write(*,130) (nbase(i),i=1,nsub),jj
                do 1100 i=1,nsub
                    mset(jj,i)=nbase(i)
1100            continue
c
c
1000        continue
c
c
            write(*,*)
130         format(10x,20(1x,i1),5x,i5)
            write(*,*)
            write(*,120) jj
120         format(1x,'Number of words=',i5)
c
c
            end
c
c           *********************************************
c           *********************************************
```

APPENDIX II

Exemplary computer program for generating
minimally cross hybridizing sets
(double stranded tag/single stranded tag complement)

```
Program 3tagN
c
c
c           Program 3tagN generates minimally cross-hybridizing
c           sets of triplex words given i) N--subunit length, (ii)
c           an initial subunit sequence, and iii) the identity
c           of the nucleotides making up the subunits, i.e.
c           whether the subunits consist of all four
c           nucleotides,
c           or some subset of nucleotides.
c
c
            character*1 sub1(20)
            integer*2 mset(10000,20), nbase(20)
c
c
            nsub=20
            ndiff=6
c
c
            write(*,*)'ENTER SUBUNIT SEQUENCE: a & g only'
            read(*,110) (sub1(k),k=1,nsub)
110         format(20a1)
c
c
c           Generate set of words differing from
c           sub1 by at least three ndiff nucleotides.
c
c
c           Translate a's & g's into numbers with a=1 & g=2
c
c
            do 800 kk=1,nsub
            if(sub1(kk).eq.'a') then
                mset(1,k)=1
            endif
                if(sub1(k).eq.'g') then
                    mset(1,kk)=2
```

APPENDIX II-continued

Exemplary computer program for generating
minimally cross hybridizing sets
(double stranded tag/single stranded tag complement)

```
                endif
800         continue
c
c
            jj=1
c
c
            do 1000 k1=1,2
            do 1000 k2=1,2
            do 1000 k3=1,2
            do 1000 k4=1,2
            do 1000 k5=1,2
            do 1000 k6=1,2
            do 1000 k7=1,2
            do 1000 k8=1,2
            do 1000 k9=1,2
            do 1000 k10=1,2
            do 1000 k11=1,2
            do 1000 k12=1,2
            do 1000 k13=1,2
            do 1000 k14=1,2
            do 1000 k15=1,2
            do 1000 k16=1,2
            do 1000 k17=1,2
            do 1000 k18=1,2
            do 1000 k19=1,2
            do 1000 k20=1,2
c
c
            nbase(1)=k1
            nbase(2)=k2
            nbase(3)=k3
            nbase(4)=k4
            nbase(5)=k5
            nbase(6)=k6
            nbase(7)=k7
            nbase(8)=k8
            nbase(9)=k9
            nbase(10)=k10
            nbase(11)=k11
            nbase(12)=k12
            nbase(13)=k13
            nbase(14)=k14
            nbase(15)=k15
            nbase(16)=k16
            nbase(17)=k17
            nbase(18)=k18
            nbase(19)=k19
            nbase(20)=k20
c
c
            do 1250 nn=1,jj
c
c
            n=0
            do 1200 j=1,nsub
                if(mset(nn,j).eq.1 .and. nbase(j).ne.1 .or.
     1          mset(nn,j).eq.2 .and. nbase(j).ne.2) then
                    n=n+1
                endif
1200        continue
c
c
            if(n.lt.ndiff) then
                goto 1000
            endif
1250        continue
c
c
            jj=jj+1
            write(*,130) (nbase(i),i=1,nsub),jj
            do 110 i=1,nsub
                mset(j,i)=nbase(i)
1100            continue
c
c
```

APPENDIX II-continued

Exemplary computer program for generating
minimally cross hybridizing sets
(double stranded tag/single stranded tag complement)

```
1000      continue
c
c
          write(*,*)
130       format(5x,20(1x,i1),5x,i5)
          write(*,*)
          write(*,120) jj
120       format(1x,'Number of words=',i5)
c
c
          end
```

---

We claim:

1. A method of determining a nucleotide sequence at an end of a polynucleotide, the method comprising the steps of:
ligating one or more encoded adaptors to the ends of identical copies of the polynucleotide, each encoded adaptor being a double stranded deoxyribonucleic acid comprising an oligonucleotide tag selected from a minimally cross-hybridizing set of oligonucleotides between 8 and 20 nucleotides or basepairs in length and a protruding strand complementary to a portion of a strand of the polynucleotide, wherein each oligonucleotide of the minimally cross-hybridizing set differs from every other oligonucleotide of the set by at least two nucleotides; and
identifying one or more nucleotides in each of said portions of the strand of the polynucleotides by specifically hybridizing a tag complement to each oligonucleotide tag of the one or more encoded adaptors ligated thereto.

2. The method of claim 1 wherein said step of ligating includes ligating a plurality of different encoded adaptors to said end of said polynucleotide such that said protruding strands of the plurality of different encoded adaptors are complementary to a plurality of different portions of said strand of said polynucleotide such that there is a one-to-one correspondence between said different encoded adaptors and the different portions of said strand.

3. The method of claim 2 wherein said different portions of said strand of said polynucleotide are contiguous.

4. The method of claim 3 wherein said protruding strand of said encoded adaptors contains from 2 to 6 nucleotides and wherein said step of identifying includes specifically hybridizing said tag complements to said oligonucleotide tags such that the identity of each nucleotide in said portions of said polynucleotide is determined successively.

5. The method of claim 4 wherein said step of identifying further includes providing a number of sets of tag complements equivalent to the number of nucleotides to be identified in said portions of said polynucleotide.

6. The method of claim 5 wherein said step of identifying further includes providing said tag complements in each of said sets that are capable of indicating the presence of a predetermined nucleotide by a signal generated by a fluorescent signal generating moiety, there being a different fluorescent signal generating moiety for each kind of nucleotide.

7. The method of claim 5 wherein said oligonucleotide tags of said encoded adaptors are single stranded and said tag complements to said oligonucleotide tags are single stranded such the specific hybridization between an oligonucleotide tag and its respective tag complement occurs through Watson-Crick base pairing.

8. The method of claim 7 wherein said encoded adaptors have the form:

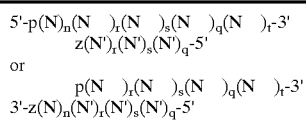

where N is a nucleotide and N' is its complement, p is a phosphate group, z is a 3' hydroxyl or a 3' blocking group, n is an integer between 2 and 6, inclusive, r is an integer between 0 and 18, inclusive, s is an integer which is either between four and six, inclusive, whenever the encoded adaptor has a nuclease recognition site or is 0 whenever there is no nuclease recognition site, q is an integer greater than or equal to 0, and t is an integer greater than or equal to 8.

9. The method of claim 8 wherein r is between 0 and 12, inclusive, t is an integer between 8 and 20, inclusive, and z is a phosphate group.

10. The method of claim 9 wherein members of said minimally cross-hybridizing set differ from every other member by at least six nucleotides.

11. The method of claim 5 wherein said oligonucleotide tags of said encoded adaptors are double stranded and said tag complements to said oligonucleotide tags are single stranded such that specific hybridization between an oligonucleotide tag and its respective tag complement occurs through the formation of a Hoogsteen or reverse Hoogsteen triplex.

12. The method of claim 11 wherein said encoded adaptors have the form:

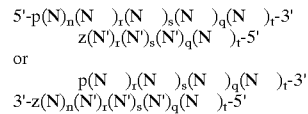

wherein N is a nucleotide and N' is its complement, p is a phosphate group, z is a 3' hydroxyl or a 3' blocking group, n is an integer between 2 and 6, inclusive, r is an integer between 0 and 18, inclusive, s is an integer which is either between four and six, inclusive, whenever the encoded adaptor has a nuclease recognition site or is 0 whenever there is no nuclease recognition site, q is an integer greater than or equal to 0, and t is an integer greater than or equal to 8.

13. The method of claim 12 wherein r is between 0 and 12, inclusive, t is an integer between 8 and 24, inclusive, and z is a phosphate group.

14. The method of claim 13 wherein members of said minimally cross-hybridizing set differ from every other member by at least six nucleotides.

15. A method of determining nucleotide sequences of a plurality of polynucleotides, the method comprising the steps of:
(a) attaching a first oligonucleotide tag from a repertoire of tags to each polynucleotide in a population of polynucleotides such that each first oligonucleotide tag from the repertoire is selected from a first minimally cross-hybridizing set of oligonucleotides between 12 and 60 nucleotides or basepairs in length and wherein each oligonucleotide of the first minimally cross hybridizing set differs from every other oligonucleotide of the first set by at least two nucleotides;
(b) sampling the population of polynucleotides to form a sample of polynucleotides such that substantially all different polynucleotides in the sample have different first oligonucleotide tags attached;
(c) sorting the polynucleotides of the sample by specifically hybridizing the first oligonucleotide tags with their respective complements, the respective complements being attached as uniform populations of substantially identical oligonucleotides in spatially discrete regions on the one or more solid phase supports;
(d) ligating one or more encoded adaptors to an end of identical copies of the polynucleotides in the sample, each encoded adaptor being a double stranded deoxyribonucleic acid comprising a second oligonucleotide tag selected from a second minimally cross-hybridizing set of oligonucleotides between 8 and 20 nucleotides or basepairs in length and a protruding strand complementary to a protruding strand of a polynucleotide of the population, wherein each oligonucleotide of the second minimally cross hybridizing set differs from every other oligonucleotide of the second set by at least two nucleotides; and (e) identifying a plurality of nucleotides in said protruding strands of the polynucleotides by specifically hybridizing a tag complement to each second oligonucleotide tag of the one or more encoded adaptors.

16. The method of claim 15 further including the steps of (f) cleaving said encoded adaptors from said polynucleotides with a nuclease having a nuclease recognition site separate from its cleavage site so that a new protruding strand is formed on said end of each of said polynucleotides, and (g) repeating steps (d) through (f).

17. A method of identifying a population of mRNA molecules, the method comprising the steps of:

(a) forming a population of cDNA molecules from the population of mRNA molecules such that each cDNA molecule has a first oligonucleotide tag attached, the first oligonucleotide tags being selected from a first minimally cross-hybridizing set of oligonucleotides between 12 and 60 nucleotides or basepairs in length and wherein each oligonucleotide of the first minimally cross hybridizing set differs from every other oligonucleotide of the first set by at least two nucleotides;

(b) sampling the population of cDNA molecules to form a sample of cDNA molecules such that substantially all different cDNA molecules have different first oligonucleotide tags attached;

(c) sorting the cDNA molecules by specifically hybridizing the first oligonucleotide tags with their respective complements, the respective complements being attached as uniform populations of substantially identical complements in spatially discrete regions on one or more solid phase supports;

(d) ligating one or more encoded adaptors to an end of the cDNA molecules in the population, each encoded adaptor being a double stranded deoxyribonucleic acid comprising a second oligonucleotide tag selected from a second minimally cross-hybridizing set of oligonucleotides between 8 and 20 nucleotides or basepairs in length and a protruding strand complementary to a protruding strand of a cDNA molecule of the sample, wherein each oligonucleotide of the second minimally cross hybridizing set differs from every other oligonucleotide of the second set by at least two nucleotides; and (e) determining the identity and ordering of a plurality of nucleotides in each of said protruding strands of the cDNA molecules by specifically hybridizing a tag complement to each second oligonucleotide tag of the one or more encoded adaptors;

wherein the population of mRNA molecules is identified by the frequency distribution of the portions of sequences of the cDNA molecules.

18. The method of claim 17 further including the steps of (f) cleaving said encoded adaptors from said polynucleotides with a nuclease having a nuclease recognition site separate from its cleavage site so that a new protruding strand is formed on said end of each of said cDNA molecules, said (g) repeating steps (d) through (f).

19. A method of determining a nucleotide sequence at an end of a polynucleotide, the method comprising the steps of:

(a) ligating an encoded adaptor to an end of the polynucleotide, the encoded adaptor being a double stranded deoxyribonucleic acid comprising an oligonucleotide tag selected from a minimally cross-hybridizing set of oligonucleotides between 8 and 20 nucleotides or basepairs in length and a protruding strand complementary to a portion of a strand of the polynucleotide, wherein each oligonucleotide of the second minimally cross hybridizing set differs from every other oligonucleotide of the second set by at least two nucleotides;

(b) identifying one or more nucleotides in the portion of the strand of the polynucleotide by specifically hybridizing a tag complement to the oligonucleotide tag of the encoded adaptor ligated thereto;

(c) cleaving the encoded adaptor from the end of the polynucleotide with a nuclease having a nuclear recognition site separate from its cleavage site so that a new protruding strand is formed at the end of the polynucleotide; and (d) repeating steps (a) through (c).

20. The method of claim 19 wherein said protruding strand of said encoded adaptor contains from 2 to 6 nucleotides and wherein step of identifying includes specifically hybridizing successive said tag complements to said oligonucleotide tag such that the identity of each nucleotide in said portion of said polynucleotide is determined successively.

21. The method of claim 20 wherein said step of identifying further includes providing a number of sets of tag complements equivalent to the number of nucleotides to be identified in said portion of said polynucleotide.

22. The method of claim 21 wherein said step of identifying further includes providing said tag complements in each of said sets that are capable of indicating the presence of a predetermined nucleotide by a signal generated by a fluorescent signal generating moiety, there being a different fluorescent signal generating moiety for each kind of nucleotide.

23. The method of claim 22 wherein said oligonucleotide tags of said encoded adaptors are single stranded and said tag complements to said oligonucleotide tags are single stranded such that specific hybridization between oligonucleotide tag and its respective tag complement occurs through Watson-Crick base pairing.

24. A composition of matter comprising a double stranded oligonucleotide adaptor having the form:

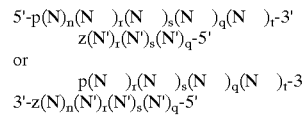

where N is a nucleotide and N' is its complement, p is a phosphate group, z is a 3' hydroxyl or a 3' blocking group, n is an integer between 2 and 6, inclusive, r is an integer between 0 and 18, inclusive, s is an integer which is either between four and six, inclusive, whenever the encoded adaptor has a nuclease recognition site or is 0 whenever there is no nuclease recognition site, q is an integer greater than or equal to 0, and t is an integer greater than or equal to 8 such that $(N)_t$ is a single stranded moiety.

25. The composition of claim 24 wherein r is between 0 and 12, inclusive, t is an integer between 8 and 20, inclusive, z is a phosphate group, and said single stranded moiety $(N)_t$ is a member of a minimally cross-hybridizing set of oligonucleotides such that each oligonucleotide of the set differs from every other oligonucleotide of the set by at least two nucleotides.

26. The composition of claim 25 wherein n equals 4 and wherein members of said minimally cross-hybridizing set differ from every other member by at least six nucleotides.

27. A composition of matter comprising a double stranded oligonucleotide adaptor having the form:

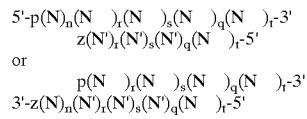

where N is a nucleotide and N' is its complement, p is a phosphate group, z is a 3' hydroxyl or a 3' blocking group, n is an integer between 2 and 6, inclusive, r is an integer between 0 and 18, inclusive, s is an integer which is either between four and six, inclusive, whenever the encoded adaptor has a nuclease recognition site or is 0 whenever there is no nuclease recognition site, q is an integer greater than or equal to 0, and t is an integer greater than or equal to 8 such that

forms a double stranded moiety selected from a minimally cross-hybridizing set of oligonucleotides such that each oligonucleotide of the set differs from every other oligonucleotide of the set by at least two basepairs.

28. The composition of claim 27 wherein r is between 0 and 12, inclusive, t is an integer between 8 and 24, inclusive, and z is a phosphate group.

29. The composition of claim 28 wherein members of said minimally cross-hybridizing set differ from every other member by at least six nucleotides.

* * * * *

SEQUENCE LISTING (1) GENERAL INFORMATION:

(iii) NUMBER OF SEQUENCES: 28

(2) INFORMATION FOR SEQ ID NO: 1:

(i) SEQUENCE CHARACTERISTICS:
      (A) LENGTH: 28 nucleotides
      (B) TYPE: nucleic acid
      (C) STRANDEDNESS: double
      (D) TOPOLOGY: linear (xi) SEQUENCE DESCRIPTION: SEQ ID NO: 1:

TGGATTCTAG AGAGAGAGAG AGAGAGAG    28

(2) INFORMATION FOR SEQ ID NO: 2:

(i) SEQUENCE CHARACTERISTICS:
      (A) LENGTH: 16 nucleotides
      (B) TYPE: nucleic acid
      (C) STRANDEDNESS: double
      (D) TOPOLOGY: linear (xi) SEQUENCE DESCRIPTION: SEQ ID NO: 2:

NNGGATGNNN NNNNNN    16

(2) INFORMATION FOR SEQ ID NO: 3:

(i) SEQUENCE CHARACTERISTICS:
      (A) LENGTH: 11 nucleotides
      (B) TYPE: nucleic acid
      (C) STRANDEDNESS: single
      (D) TOPOLOGY: linear (xi) SEQUENCE DESCRIPTION: SEQ ID NO: 3:

NRRGATCYNN N    11

(2) INFORMATION FOR SEQ ID NO: 4:

(i) SEQUENCE CHARACTERISTICS:
      (A) LENGTH: 20 nucleotides
      (B) TYPE: nucleic acid
      (C) STRANDEDNESS: double
      (D) TOPOLOGY: linear (xi) SEQUENCE DESCRIPTION: SEQ ID NO: 4:

AGTGGCTGGG CATCGGACCG    20

(2) INFORMATION FOR SEQ ID NO: 5:

(i) SEQUENCE CHARACTERISTICS:
        (A) LENGTH: 20 nucleotides
        (B) TYPE: nucleic acid
        (C) STRANDEDNESS: double
        (D) TOPOLOGY: linear (xi) SEQUENCE DESCRIPTION: SEQ ID NO: 5:

```
GGGGCCCAGT CAGCGTCGAT                                              20
```

(2) INFORMATION FOR SEQ ID NO: 6:

(i) SEQUENCE CHARACTERISTICS:
        (A) LENGTH: 70 nucleotides
        (B) TYPE: nucleic acid
        (C) STRANDEDNESS: double
        (D) TOPOLOGY: linear (xi) SEQUENCE DESCRIPTION: SEQ ID NO: 6:

```
AAAAGGAGGA GGCCTTGATA GAGAGGACCT GTTTAAACGT TTAAACGGAT             50

CCTCTTCCTC TTCCTCTTCC                                              70
```

(2) INFORMATION FOR SEQ ID NO: 7:

(i) SEQUENCE CHARACTERISTICS:
        (A) LENGTH: 34 nucleotides
        (B) TYPE: nucleic acid
        (C) STRANDEDNESS: single
        (D) TOPOLOGY: linear (xi) SEQUENCE DESCRIPTION: SEQ ID NO: 7:

```
CTAAACCATT GGTATGGGCC AGTGAATTGT AATA                              34
```

(2) INFORMATION FOR SEQ ID NO: 8:

(i) SEQUENCE CHARACTERISTICS:
        (A) LENGTH: 55 nucleotides
        (B) TYPE: nucleic acid
        (C) STRANDEDNESS: single
        (D) TOPOLOGY: linear (xi) SEQUENCE DESCRIPTION: SEQ ID NO: 8:

```
CGCGCAGCCC GCATCGTTTA TGCTACAGAC TGTCAGTGCA                        40

GCTCTCCGAT CCAAA                                                   55
```

(2) INFORMATION FOR SEQ ID NO: 9:

(i) SEQUENCE CHARACTERISTICS:
        (A) LENGTH: 16 nucleotides
        (B) TYPE: nucleic acid
        (C) STRANDEDNESS: double
        (D) TOPOLOGY: linear (xi) SEQUENCE DESCRIPTION: SEQ ID NO: 9:

```
TCGATGGGCT AGATTT                                                  16
```

(2) INFORMATION FOR SEQ ID NO: 10:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 10:

ANNNTACAGC TGCATCCCTT GGCGCTGAGG                               30

(2) INFORMATION FOR SEQ ID NO: 11:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 11:

NANNTACAGC TGCATCCCTG GGCCTGTAAG                               30

(2) INFORMATION FOR SEQ ID NO: 12:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 12:

CNNNTACAGC TGCATCCCTT GACGGGTCTC                               30

(2) INFORMATION FOR SEQ ID NO: 13:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 13:

NCNNTACAGC TGCATCCCTG CCCGCACAGT                               30

(2) INFORMATION FOR SEQ ID NO: 14:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 14:

GNNNTACAGC TGCATCCCTT CGCCTCGGAC                               30

(2) INFORMATION FOR SEQ ID NO: 15:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 15:

NGNNTACAGC TGCATCCCTG ATCCGCTAGC                               30

(2) INFORMATION FOR SEQ ID NO: 16:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 16:

TNNNTACAGC TGCATCCCTT CCGAACCCGC                               30

(2) INFORMATION FOR SEQ ID NO: 17:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 17:

NTNNTACAGC TGCATCCCTG AGGGGGATAG                                              30

(2) INFORMATION FOR SEQ ID NO: 18:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 18:

NNANTACAGC TGCATCCCTT CCCGCTACAC                                              30

(2) INFORMATION FOR SEQ ID NO: 19:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 19:

NNNATACAGC TGCATCCCTG ACTCCCCGAG                                              30

(2) INFORMATION FOR SEQ ID NO: 20:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 20:

NNCNTACAGC TGCATCCCTG TGTTGCGCGG                                              30

(2) INFORMATION FOR SEQ ID NO: 21:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 21:

NNNCTACAGC TGCATCCCTC TACAGCAGCG                                              30

(2) INFORMATION FOR SEQ ID NO: 22:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 22:

NNGNTACAGC TGCATCCCTG TCGCGTCGTT                                              30

(2) INFORMATION FOR SEQ ID NO: 23:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 23:

NNNGTACAGC TGCATCCCTC GGAGCAACCT          30

(2) INFORMATION FOR SEQ ID NO: 24:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 24:

NNTNTACAGC TGCATCCCTG GTGACCGTAG          30

(2) INFORMATION FOR SEQ ID NO: 25:

(i) SEQUENCE CHARACTERISTICS:
        (A) LENGTH: 30 nucleotides
        (B) TYPE: nucleic acid
        (C) STRANDEDNESS: double
        (D) TOPOLOGY: linear (xi) SEQUENCE DESCRIPTION: SEQ ID NO: 25:

NNNTTACAGC TGCATCCCTC CCCTGTCGGA          30

(2) INFORMATION FOR SEQ ID NO: 26:

(i) SEQUENCE CHARACTERISTICS:
        (A) LENGTH: 78 nucleotides
        (B) TYPE: nucleic acid
        (C) STRANDEDNESS: single
        (D) TOPOLOGY: linear (xi) SEQUENCE DESCRIPTION: SEQ ID NO: 26:

ACTAATCGTC TCACTATTTA ATTAANNNNN NNNNNNNNNN          40

NNNNNNNNNN NNNNNNNGGT TTTTTTTTTT TTTTTTTV            78

(2) INFORMATION FOR SEQ ID NO: 27:

(i) SEQUENCE CHARACTERISTICS:
        (A) LENGTH: 17 nucleotides
        (B) TYPE: nucleic acid
        (C) STRANDEDNESS: double
        (D) TOPOLOGY: linear (xi) SEQUENCE DESCRIPTION: SEQ ID NO: 27:

ATAGGGGTCT TCGGTAC          17

(2) INFORMATION FOR SEQ ID NO: 28:

(i) SEQUENCE CHARACTERISTICS:
        (A) LENGTH: 19 nucleotides
        (B) TYPE: nucleic acid
        (C) STRANDEDNESS: double
        (D) TOPOLOGY: linear (xi) SEQUENCE DESCRIPTION: SEQ ID NO: 28:

GATCAGCTGC TGCAAATTT          19